(12) United States Patent
Jaber et al.

(10) Patent No.: US 12,224,064 B2
(45) Date of Patent: Feb. 11, 2025

(54) DEEP LEARNING MODELS FOR TUMOR EVALUATION

(71) Applicants: NantCell, Inc., Culver City, CA (US); NantOmics, LLC, Culver City, CA (US); NantHealth, Inc., Culver City, CA (US)

(72) Inventors: Mustafa I. Jaber, Los Angeles, CA (US); Christopher W. Szeto, Culver City, CA (US); Liudmila A. Beziaeva, Culver City, CA (US); Stephen Charles Benz, Culver City, CA (US)

(73) Assignees: NantCell, Inc., Culver City, CA (US); NantOmics, LLC, Culver City, CA (US); NantHealth, Inc., Culver City, CA (US)

( * ) Notice: Subject to any disclaimer, the term of this patent is extended or adjusted under 35 U.S.C. 154(b) by 338 days.

(21) Appl. No.: 17/789,590

(22) PCT Filed: Jan. 11, 2021

(86) PCT No.: PCT/US2021/012980
§ 371 (c)(1),
(2) Date: Jun. 28, 2022

(87) PCT Pub. No.: WO2021/142449
PCT Pub. Date: Jul. 15, 2021

(65) Prior Publication Data
US 2023/0030506 A1    Feb. 2, 2023

Related U.S. Application Data

(60) Provisional application No. 62/959,931, filed on Jan. 11, 2020.

(51) Int. Cl.
G16H 50/20    (2018.01)
G06F 18/2413    (2023.01)
(Continued)

(52) U.S. Cl.
CPC ......... G16H 50/20 (2018.01); G06F 18/2413 (2023.01); G06T 7/0012 (2013.01);
(Continued)

(58) Field of Classification Search
CPC ..................................................... G06T 11/206
See application file for complete search history.

(56) References Cited

U.S. PATENT DOCUMENTS

2016/0201149 A1* 7/2016 Kim ..................... C12Q 1/6841
435/5
2017/0352157 A1* 12/2017 Madabhushi .......... G16H 30/40
(Continued)

FOREIGN PATENT DOCUMENTS

WO    WO-2019108888 A1    6/2019
WO    WO-2019133538 A3 *    3/2020    ............. G06N 20/00

OTHER PUBLICATIONS

International Search Report from corresponding PCT Application No. PCT/US2021/012980 dated Apr. 22, 2021.
(Continued)

Primary Examiner — Di Xiao
(74) Attorney, Agent, or Firm — Harness Dickey & Pierce P.L.C.

(57) ABSTRACT

A method of determining a clinical value for an individual based on a tumor in an image by an apparatus including processing circuitry may include executing, by the processing circuitry, instructions that cause the apparatus to determine a lymphocyte distribution of lymphocytes in the tumor based on the image; apply a classifier to the lymphocyte distribution to classify the tumor, the classifier having been trained to classify tumors into a class selected from at least two classes respectively associated with lymphocyte distributions; and determine the clinical value for the individual
(Continued)

based on prognoses of individuals with tumors in the class into which the classifier classified the tumor.

16 Claims, 21 Drawing Sheets

(51) Int. Cl.
*G06T 7/00* (2017.01)
*G06V 20/69* (2022.01)
*G16H 30/40* (2018.01)

(52) U.S. Cl.
CPC ............ *G06V 20/69* (2022.01); *G06V 20/698* (2022.01); *G16H 30/40* (2018.01)

(56) References Cited

U.S. PATENT DOCUMENTS

| | | | |
|---|---|---|---|
| 2017/0365053 A1* | 12/2017 | Yuan ...................... | G06T 7/0012 |
| 2018/0230435 A1* | 8/2018 | Yang ................ | G01N 33/57492 |
| 2019/0188853 A1* | 6/2019 | Schirman ................ | G06T 7/136 |
| 2021/0017275 A1* | 1/2021 | Monroe .................. | A61P 29/00 |
| 2021/0238690 A1* | 8/2021 | Würfel ................. | C12Q 1/6886 |

OTHER PUBLICATIONS

Written Opinion from corresponding PCT Application No. PCT/US2021/012980 dated Apr. 22, 2021.
Saltz, J., et al., "Spatial Organization and Molecular Correlation of Tumor-Infiltrating Lymphocytes Using Deep Learning on Pathology Images," Cell Rep., 23(1): 181-193 (2018).

\* cited by examiner

| Step 0 | Silhouette score | C-index |
|---|---|---|
| f0 | 0.4994 | 0.3363 |
| f1 | 0.5970 | 0.5175 |
| f2 | 0.4712 | 0.5215 |
| f3 | 0.5837 | 0.4393 |
| f4 | 0.6577 | 0.3574 |
| f5 | 0.5649 | 0.5117 |
| f6 | 0.5680 | 0.4987 |
| f7 | 0.6098 | 0.3662 |
| f8 | 0.6305 | 0.4137 |

| Step 1 | Silhouette score | C-index |
|---|---|---|
| f4f0 | 0.4955 | 0.5319 |
| f4f1 | 0.4548 | 0.5123 |
| f4f2 | 0.5443 | 0.4731 |
| f4f3 | 0.4643 | 0.6234 |
| f4f5 | 0.4728 | 0.5123 |
| f4f6 | 0.3837 | 0.5123 |
| f4f7 | 0.5795 | 0.4843 |
| f4f8 | 0.5157 | 0.4960 |

| Step 2 | Silhouette score | C-index |
|---|---|---|
| f4f7f0 | 0.4799 | 0.5296 |
| f4f7f1 | 0.3782 | 0.4450 |
| f4f7f2 | 0.5115 | 0.4731 |
| f4f7f3 | 0.5334 | 0.5006 |
| f4f7f5 | 0.4424 | 0.4843 |
| f4f7f6 | 0.3782 | 0.5123 |
| f4f7f8 | 0.4552 | 0.5048 |

| Step 3 | Silhouette score | C-index |
|---|---|---|
| f4f7f3f0 | 0.4352 | 0.5319 |
| f4f7f3f1 | 0.4305 | 0.4843 |
| f4f7f3f2 | 0.4921 | 0.5790 |
| f4f7f3f05 | 0.3886 | 0.6117 |
| f4f7f3f06 | 0.3280 | 0.6234 |
| f4f7f3f8 | 0.3628 | 0.4983 |

| Step 4 | Silhouette score | C-index |
|---|---|---|
| f4f7f3f2f0 | 0.4693 | 0.4797 |
| f4f7f3f2f1 | 0.3795 | 0.6124 |
| f4f7f3f2f5 | 0.4259 | 0.5790 |
| f4f7f3f2f6 | 0.3352 | 0.5842 |
| f4f7f3f2f8 | 0.2757 | 0.4679 | f0 = 'percent_of_tissue_is_tumor'
f1 = 'percent_of_tissue_is_stroma'
f2 = 'percent_of_tissue_is_lymphocytes'
f3 = 'percent_lymphocytes_within_100um_from_tumor'
f4 = 'percent_lymphocytes_within_200um_from_tumor'
f5 = 'percent_lymphocytes_within_100um_from_stroma'
f6 = 'percent_lymphocytes_within_200um_from_stroma'
f7 = 'percent_stroma_within_100um_from_tumor'
f8 = 'percent_stroma_within_200um_from_tumor'

FIG. 7

| | | f4 = percent of lymphocytes within 200um from tumor | f7 = percent of stroma within 100um from tumor | f3 = percent of lymphocytes within 100um from tumor | f2 = percent of tissue that is lymphocytes |
|---|---|---|---|---|---|
| Low risk | TCGA-HZ-A8P1-01Z-00-DX1 | 45.4545 | 2.1668 | 9.0909 | 0.4604 |
| | TCGA-F2-A7TX-01Z-00-DX1 | 96.6265 | 38.6619 | 69.4284 | 16.2899 |
| | TCGA-OE-A75W-01Z-00-DX1 | 83.7061 | 16.8822 | 46.4058 | 8.3184 |
| High risk | TCGA-3A-A9IZ-01Z-00-DX1 | 53.1876 | 12.1540 | 17.1828 | 8.1839 |
| | TCGA-IB-A5SO-01Z-00-DX1 | 54.3373 | 5.2897 | 18.1928 | 3.5219 |

FIG. 8

| Step 0 | |
|---|---|
| Clinical and exposure features | P value |
| ajcc_pathologic_t | 0.0006 |
| ajcc_pathologic_n | 0.0025 |
| race | 0.0034 |
| ethnicity | 0.0072 |
| treatment_or_therapy | 0.0269 |
| site_of_resection_or_biopsy | 0.0522 |
| cigarettes_per_day | 0.0991 |
| ajcc_pathologic_m | 0.1560 |
| prior_malignancy | 0.2240 |
| years_smoked | 0.2519 |
| primary_diagnosis | 0.2614 |
| alcohol_history | 0.6284 |
| gender | 0.7065 |

1002-1

| Step 1 | |
|---|---|
| Clinical features | P value |
| ajcc_pathologic_n | 0.0022 |
| ajcc_pathologic_t | 0.0028 |
| ethnicity | 0.0295 |
| treatment_or_therapy | 0.0348 |
| race | 0.0655 |

1002-2

| Step 2 | |
|---|---|
| Clinical features | P value |
| ajcc_pathologic_n | 0.0026 |
| ajcc_pathologic_t | 0.0052 |
| ethnicity | 0.0563 |
| treatment_or_therapy | 0.0567 |

1002-3

| Step 3 | |
|---|---|
| Clinical features | P value |
| ajcc_pathologic_n | 0.0079 |
| ajcc_pathologic_t | 0.0750 |

1002-4

| | HR | P value | Low Risk N | High Risk N |
|---|---|---|---|---|
| training set | 0.2182 | 0.0200 | 8 | 42 |
| test set | 0.4065 | 0.2855 | 2 | 30 |

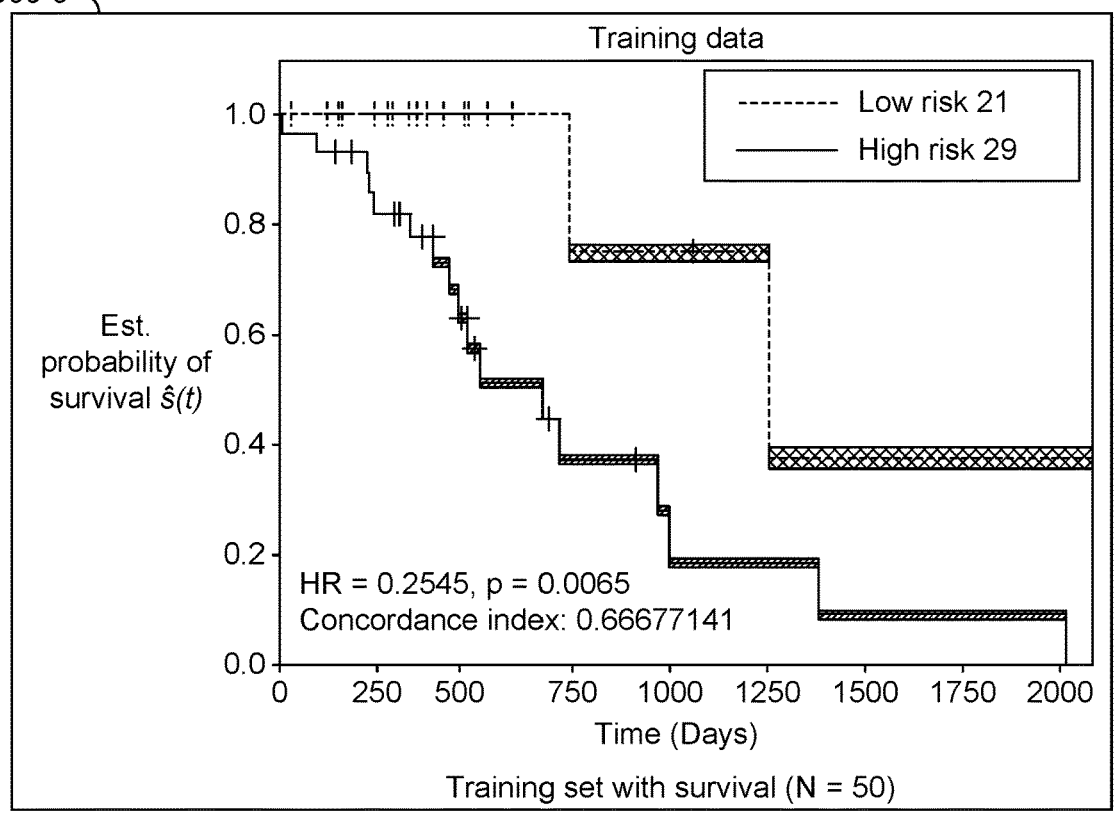
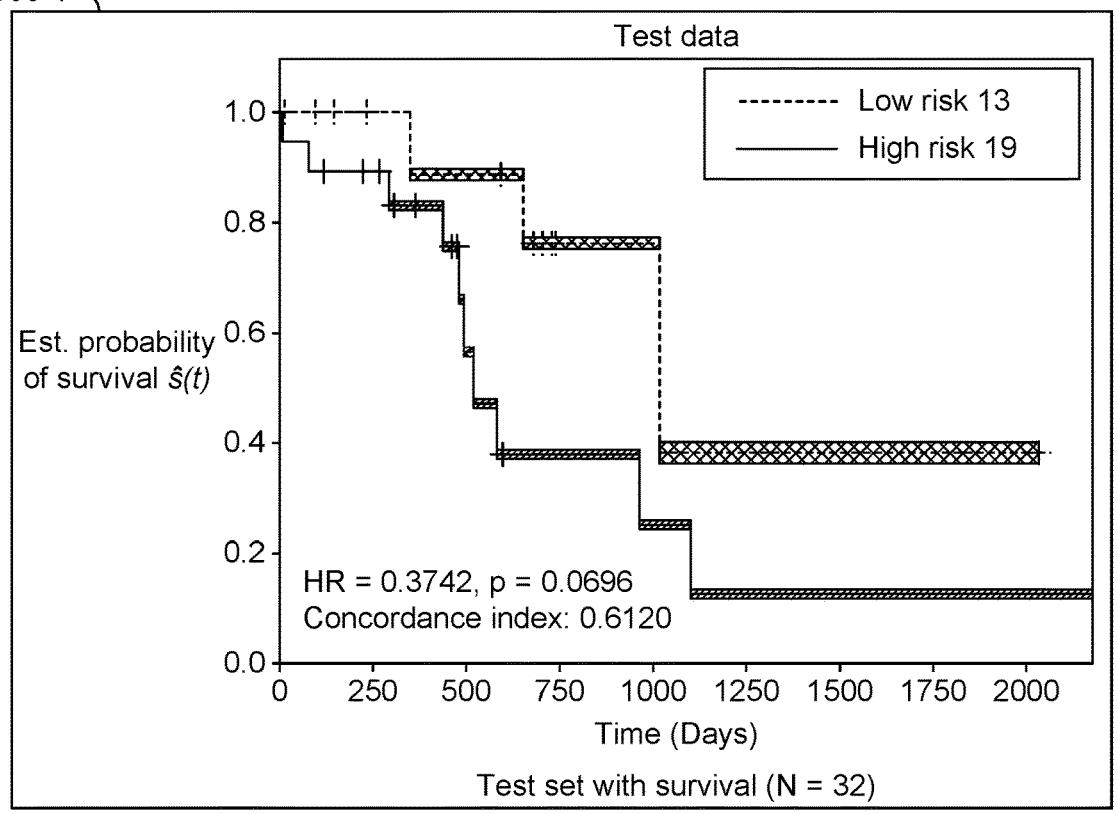
FIG. 11

| Image-based tumor, stroma, and lymphocytes spatial features | | | | | |
|---|---|---|---|---|---|
| | HR | P value | C-index | Low Risk N | High Risk N |
| training set | 0.5117 | 0.0570 | 0.6667 | 24 | 26 |
| test set | 0.5154 | 0.0936 | 0.5964 | 21 | 11 |

| Selected clinical features | | | | | |
|---|---|---|---|---|---|
| | HR | P value | C-index | Low Risk N | High Risk N |
| training set | 0.2182 | 0.0200 | 0.6564 | 8 | 42 |
| test set | 0.4065 | 0.2855 | 0.5651 | 2 | 30 |

| Image and clinical features | | | | | |
|---|---|---|---|---|---|
| | HR | P value | C-index | Low Risk N | High Risk N |
| training set | 0.2545 | 0.0065 | 0.7141 | 21 | 29 |
| test set | 0.3742 | 0.0696 | 0.6120 | 13 | 19 |

FIG. 12

DEEP LEARNING MODELS FOR TUMOR EVALUATION

CROSS-REFERENCE TO RELATED APPLICATIONS

This application is a National Stage of International Application No. PCT/US2021/012980, filed Jan. 11, 2021, which claims the benefit of U.S. Provisional Application No. 62/959,931 filed Jan. 11, 2020, the entire disclosures of which are incorporated herein by reference.

FIELD

The present disclosure relates to the field of image analysis using machine learning models, and more particularly to determining clinical variables related to tumors using deep learning models.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

In the field of medicine, many scenarios involve an analysis of cancer tumors to evaluate a tumor class based on characteristics such as location, size, shape, and composition. The evaluation may enable predictions such as the tumor behavior and likely aggressiveness, such as the probability and rate of growth and/or metastasis. These properties of the tumor may in turn enable determinations about the clinical value (such as the prognosis) for the individual, such as the likely survival rate, and may guide decisions about medical treatment, such as a selection, type, and/or timing of chemotherapy, surgery, and palliative care. However, the determination of prognosis, including survivability, is difficult to the number and variety of relevant factors and factor correlations that may affect this determination.

A wide variety of diagnostic and prognostic techniques may be used to perform the evaluation of tumor classes. For example, a collection of data may include features about individuals with tumors, such as each individual's age, physiology, medical history, and/or behaviors such as smoking, may be correlated with prognostic data of the individual, such as typical survival rates. A Cox proportional hazards models may be applied to determine the correlation of features of a clinical feature set based on the collected data set and the clinical data, which may support some conclusions about the relevance of respective risk factors for the clinical value (such as the prognosis) for the individual based on the tumor. Clinicians may thereafter use this information to guide determinations or predictions about the diagnosis, prognosis, and/or effective care options for individuals with similar tumors. Also, similar risk factors may be collected about such individuals and processed through the Cox proportional hazards model to predict the clinical value (such as the prognosis) for the individual based on similar tumors upon which the Cox proportional hazards model was developed.

Other techniques for evaluating the clinical value (such as the prognosis) for an individual based on a tumor may utilize one or more machine learning models. For example, a training data set of tumor samples with known properties, such as data about the tumor, the individual from whom the tumor were removed, and/or the clinical value (such as the prognosis) for the individual, may be generated. A machine learning classifier may be trained using the training data set with labels that indicate the classes represented by each input, such as whether each tumor represents a high-risk tumor with a poor prognosis or a low-risk tumor with a good prognosis. The training process may result in a trained machine learning classifier that classifies new input in a manner that is consistent with the examples of the training data set.

A variety of different machine learning models may be selected as classifiers for tumors, such as Bayesian classifiers, artificial neural networks, and support vector machines (SVMs). As a first such example, a convolutional neural network (CNN) may process an n-dimensional input to detect features of images of tumors that may occur therein. A feature vector, such as a pixel array of an image of a tumor, may be provided to a convolutional neural network including a sequence of convolutional layers of neurons. Each convolutional layer may produce a feature map indicating some image features of the tumor that were detected at a level of detail, which may be processed by a next convolutional layer in the sequence. The feature map produced by the final convolutional layer of the convolutional neural network may be processed by a classifier of the tumor, which may be trained to indicate whether the feature map is similar to the feature maps of objects in the images of the training data set. For example, the CNN may be trained to identify visual features of a tumor that are correlated with high-risk and low-risk prognoses.

As a second such example, a Gaussian Mixture Model (GMM) may be generated to classify data about tumors into different clusters of tumors with representative properties. For each sample in the training data set representing a tumor, a set of features may be identified, such as location, size, shape, and composition. The samples of the training data set may be positioned within a multidimensional feature space, where each feature is represented along a dimensional axis. Machine learning techniques may be applied to identify clusters of tumors within the feature space that share a similar prognosis, such as a first cluster representing high-risk tumors and second cluster representing low-risk tumors, where each cluster is represented as a collection of Gaussian probability distributions of the respective features within the feature space. Even if some parts of the clusters overlap (for example, even if a tumor with particular set of features could be included in either the high-risk cluster or the low-risk cluster), the Gaussian probability distributions of the clusters may enable a probabilistic prediction as to the likelihood of the tumor belonging to each cluster. In this manner, the Gaussian mixture model may enable individual prognosis prediction based on clustering of similar tumor samples in the training data set.

BRIEF SUMMARY

Some example embodiments may include a method of operating an apparatus including processing circuitry, in which the method includes executing, by the processing circuitry, instructions that cause the apparatus to receive an image depicting at least part of a tumor, determine a lymphocyte distribution of lymphocytes in the tumor based on the image, apply a classifier to the lymphocyte distribution to classify the tumor, the classifier having been trained to classify tumors into a class selected from at least two classes respectively associated with lymphocyte distributions, and determine a clinical value for an individual based on a set of prognosis data corresponding to individuals with tumors in the class into which the classifier classified the tumor.

In some example embodiments, the tumor is a pancreatic adenocarcinoma tumor or a breast cancer tumor.

In some example embodiments, the apparatus may further include a convolutional neural network that is trained to determine a lymphocyte distribution of lymphocytes in an area of an image, and the instructions may cause the apparatus to invoke the convolutional neural network to determine the lymphocyte distribution of lymphocytes in respective areas of the image of the tumor. In some example embodiments, the convolutional neural network may be further trained to classify an area of the image as one or more area types selected from an area type set including, a tumor area, a lymphocyte area, or a stroma area. In some example embodiments, determining the lymphocyte distribution of lymphocytes in the tumor may include, for respective lymphocyte areas of the image and determining a distance of the lymphocyte area to one or both of a tumor area or a stroma area, based on the distance, characterizing the lymphocyte area as one of, a tumor-infiltrating lymphocyte area, a tumor-adjacent lymphocyte area, a stroma-infiltrating lymphocyte area, or a stroma-adjacent lymphocyte area, and the classifier may further classify the tumor based on the characterizing of the lymphocyte area. In some example methods, determining the lymphocyte distribution of lymphocytes in the tumor may include, for respective stroma areas of the image, determining a distance of the stroma area to a tumor area, and based on the distance, characterizing the stroma area as one of, a tumor-infiltrating stroma area, or a tumor-adjacent stroma area, and the classifier may further classify the tumor based on the characterizing of the stroma area.

In some example embodiments, the at least two classes may include, a high-risk class of tumors that are associated with a first survival probability, and a low-risk class of tumors that are associated with a second survival probability that is longer than the first survival probability.

In some example embodiments, the classifier may further include a Gaussian mixture model configured to determine, for respective classes, a probability distribution of features for tumors in the class within a feature space. In some example embodiments, the features of the feature space of the Gaussian mixture model may be selected from a feature set including, a measurement of tumor areas of the image, a measurement of stroma areas of the image, a measurement of lymphocyte areas of the image, a measurement of tumor-infiltrating lymphocyte areas of the image, a measurement of tumor-adjacent lymphocyte areas of the image, a measurement of stroma-infiltrating lymphocyte areas of the image, a measurement of stroma-adjacent lymphocyte areas of the image, a measurement of tumor-infiltrating stroma areas of the image, and a measurement of tumor-adjacent stroma areas of the image. In some example embodiments, from the feature set, a feature subset may be selected based on a correlation of the respective classes with respective features of the subset. In some example embodiments, the correlation of the respective classes with the respective features may be based on one or both of, a silhouette score of the feature space, or a concordance index. In some example embodiments, the feature subset may consist essentially of, the measurement of lymphocyte areas of the image, the measurement of tumor-infiltrating lymphocyte areas of the image, the measurement of tumor-adjacent lymphocyte areas of the image, and the measurement of tumor-infiltrating stroma areas of the image.

In some example embodiments, the instructions may further cause the apparatus to, apply a Cox proportional hazards model to clinical features of the tumor to determine a class of the tumor, and determine the clinical value (such as the prognosis) for the individual based on the prognoses for the individuals with tumors in the class into which the classifier classified the tumor and the class determined by the Cox proportional hazards model. In some example embodiments, the clinical features of the tumor of the Cox proportional hazards model may be selected from a clinical feature set including a primary diagnosis of the tumor, a location of the tumor, a treatment of the tumor, a measurement of the tumor, a metastatic condition of the tumor, a primary diagnosis for the individual, a previous cancer medical history of the individual, a race of the individual, an ethnicity of the individual, a gender of the individual, a smoking habit frequency of the individual, a smoking habit duration of the individual, an alcohol history of the individual. In some example embodiments, from the clinical feature set, a clinical feature subset of clinical features may be selected for the Cox proportional hazards model based on a correlation of the respective classes with respective clinical features of the subset. In some example embodiments, the clinical feature subset may consist of, the measurement of the tumor, and the metastatic condition of the tumor.

In some example embodiments, the instructions may further cause the apparatus to display a visualization of a clinical value (such as a prognosis) for the individual. In some example embodiments, the visualization is a Kaplan Meier survivability projection of the tumor. In some example embodiments, the instructions may further cause the apparatus to determine a diagnostic test for the tumor based on the clinical value (such as the prognosis) for the individual. In some example embodiments, the instructions may further cause the apparatus to determine a treatment of the individual based on the clinical value (such as the prognosis) for the individual. In some example embodiments, the instructions may further cause the apparatus to determine a schedule of a therapeutic agent for treating the tumor based on the clinical value (such as the prognosis) for the individual.

In some example embodiments, the at least two classes are a low-risk tumor class and a high-risk tumor class, determining the lymphocyte distribution further includes applying a convolutional neural network to the image, the convolutional neural network configured to measure the lymphocyte distribution of lymphocytes for different area types of the image, the classifier is a two-way Gaussian mixture model configured to determine, for respective classes, a probability distribution of features for tumors in the class within a feature space, the method further includes applying a Cox proportional hazards model to clinical features of the tumor to determine the class of the tumor, and determining the clinical value (such as the prognosis) for the individual is further based on the class predicted by the Cox proportional hazards model.

Some example embodiments may include a system including memory hardware configured to store instructions that embody any of the above methods, and processing hardware configured to execute the instructions stored by the memory hardware.

Some example embodiments may include a system including an image evaluator configured to determine a lymphocyte distribution of lymphocytes in an image, a classifier configured to classify tumors into a class selected from at least two classes respectively associated with lymphocyte distributions and a tumor evaluator configured to determine a clinical value (such as a prognosis and/or survivability) for an individual based on a tumor in an image by, invoking the image evaluator with the image to determine the lymphocyte distribution of lymphocytes in the tumor, invoking the classifier to classify the tumor into a class based on the lymphocyte distribution, and outputting a clinical value (such as a prognosis) for the individual based on prognoses of individuals with tumors in the class into which the classifier classified the tumor. In some example embodiments, the at least two classes are a low-risk tumor class and a high-risk tumor class, the image evaluator is a convolutional neural network configured to measure the lymphocyte distribution of lymphocytes for different area types of the image, the classifier is a two-way Gaussian mixture model configured to determine, for respective classes, a probability distribution of features for tumors in the class within a feature space, the system further includes a Cox proportional hazards model to clinical features of the tumor to determine a class of the tumor, and the tumor evaluator is further configured to determine the clinical value (such as the prognosis) for the individual based on the prognoses of the individuals with tumors in the class into which the classifier classified the tumor and the class determined by the Cox proportional hazards model.

Some example embodiments may include a system including image evaluating means for determining a lymphocyte distribution of lymphocytes in an image, classifying means for classifying tumors into a class selected from at least two classes respectively associated with lymphocyte distributions, and tumor evaluator means for determining a clinical value (such as a prognosis) for an individual based on a tumor in an image by, invoking the image evaluating means with the image to determine the lymphocyte distribution of lymphocytes in the tumor, invoking the classifier to classify the tumor into a class based on the lymphocyte distribution, and outputting a clinical value (such as a prognosis) for the individual based on prognoses of individuals with tumors in the class into which the classifier classified the tumor.

Some example embodiments may include an apparatus including a memory storing instructions, and processing circuitry configured by execution of the instructions stored in the memory to determine a clinical value (such as a prognosis) for an individual based on a tumor in an image by, determining a lymphocyte distribution of lymphocytes in a tumor based on an image of the tumor, applying a classifier to the lymphocyte distribution to classify the tumor, the classifier configured to classify tumors into a class selected from at least two classes respectively associated with lymphocyte distributions, and outputting a clinical value (such as a prognosis) for the individual based on prognoses of individuals with tumors in the class into which the classifier classified the tumor. In some example embodiments, the at least two classes are a low-risk tumor class and a high-risk tumor class, determining the lymphocyte distribution further includes applying a convolutional neural network to the image, the convolutional neural network configured to measure the lymphocyte distribution of lymphocytes for different area types of the image, the classifier includes a two-way Gaussian mixture model configured to determine, for respective classes, a probability distribution of features for tumors in the class within a feature space, and the instructions further cause the processing circuitry to apply a Cox proportional hazards model to clinical features of the tumor to determine a class of the tumor, and determine the clinical value (such as the prognosis) for the individual based on the prognoses of the individuals with tumors in the class into which the classifier classified the tumor and the class determined by the Cox proportional hazards model.

Some example embodiments may include a non-transitory computer-readable medium storing instructions that, when executed by processing circuitry, cause the processing circuitry to determine a clinical value (such as a prognosis) for an individual based on a tumor in an image by, determining a lymphocyte distribution of lymphocytes in a tumor based on an image of the tumor, applying a classifier to the lymphocyte distribution to classify the tumor, the classifier configured to classify tumors into a class selected from at least two classes respectively associated with lymphocyte distributions, and outputting a clinical value (such as a prognosis) for the individual based on prognoses of individuals with tumors in the class into which the classifier classified the tumor. In some example embodiments, the at least two classes are a low-risk tumor class and a high-risk tumor class, determining the lymphocyte distribution further includes applying a convolutional neural network to the image, the convolutional neural network configured to measure the lymphocyte distribution of lymphocytes for different area types of the image, the classifier includes a two-way Gaussian mixture model configured to determine, for respective classes, a probability distribution of features for tumors in the class within a feature space, and the instructions further cause the processing circuitry to apply a Cox proportional hazards model to clinical features of the tumor to determine a class of the tumor, and determine the clinical value (such as the prognosis) for the individual based on the prognoses of the individuals with tumors in the class into which the classifier classified the tumor and the class determined by the Cox proportional hazards model.

BRIEF DESCRIPTION OF THE DRAWINGS

The present disclosure will become more fully understood from the detailed description and the accompanying drawings. In the drawings, reference numbers may be reused to identify similar and/or identical elements.

FIG. 7 is an illustration of a selection of a feature subset for a classifier from a feature set of features within a feature space based on a correlation of respective features with respective classes in accordance with some example embodiments.

FIG. 8 is an illustration of a classification of tumors of different classes based on a feature subset in accordance with some example embodiments.

FIG. 10 is an illustration of a selection of a clinical feature subset for a Cox proportional hazards model from a clinical feature set of clinical features within a feature space based on a correlation of respective features with respective classes in accordance with some example embodiments.

FIG. 11 is an illustration of a Kaplan Meier survivability plot based on image analysis and a Cox proportional hazards model in accordance with some example embodiments.

FIG. 12 is an illustration of a result set of a classification of a tumor training data set and a tumor test data set based on an image analysis and a Cox proportional hazards model in accordance with some example embodiments.

DETAILED DESCRIPTION

A. Introduction

The following introduction is intended to provide an overview of some machine learning features that relate to some example embodiments.

Figure 1:
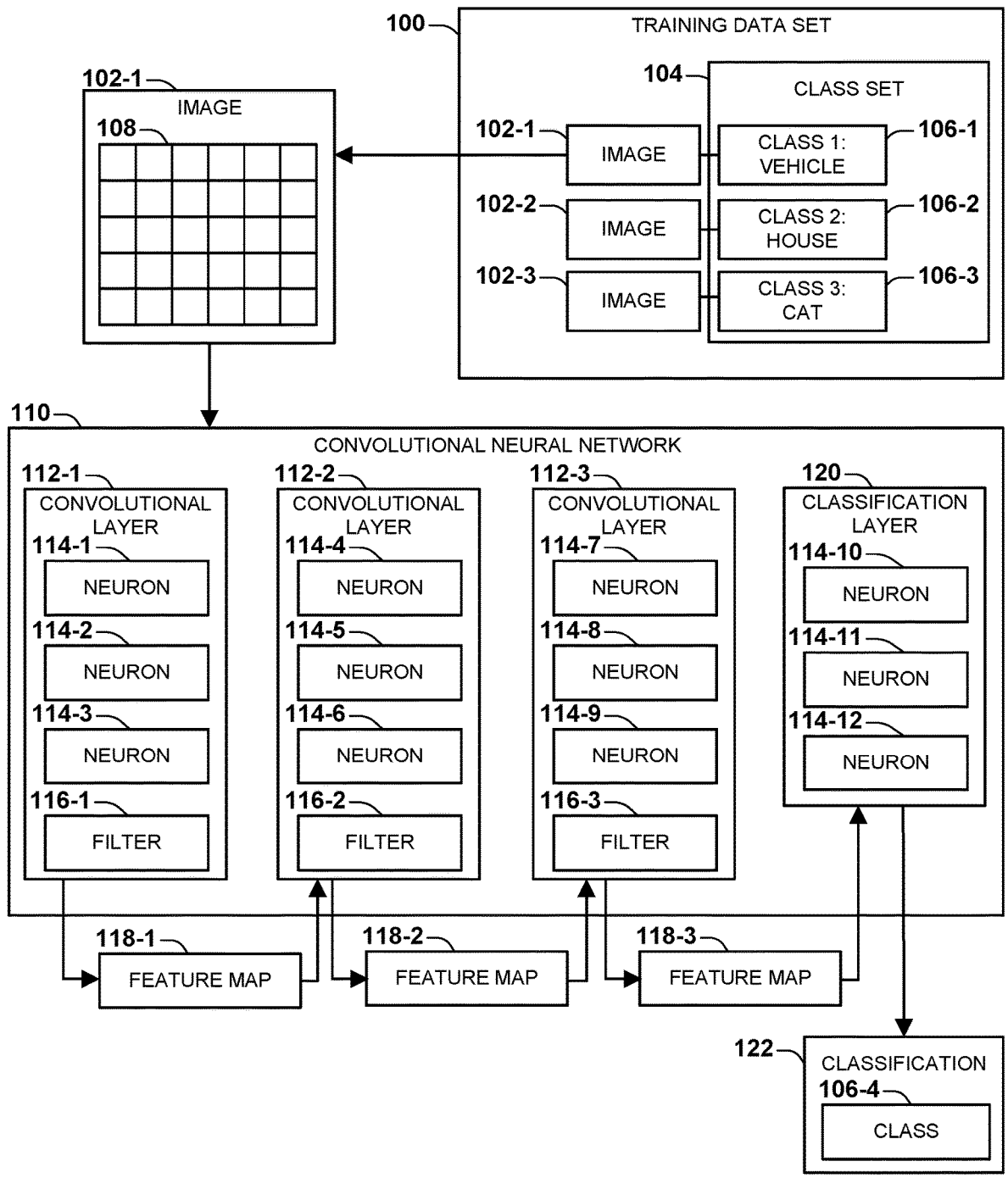
FIG. 1 is an illustration of an example convolutional neural network.

FIG. 1 is an example of a convolutional neural network (CNN) 110 that is trained to process an n-dimensional input to detect a number of features.

In the example of FIG. 1, the convolutional neural network 110 processes images 102 as a two-dimensional array of pixels 108 in one or more colors, but some such convolutional neural networks 110 may process other forms of data, such as sound, text, or a signal from a sensor.

In the example of FIG. 1, a training data set 100 is provided as a set of images 102 that are each associated with a class 106 from a class set 104. For example, the training data set 100 may include a first image 102-1 of a vehicle that is associated with a first class 106-1 for images of vehicles; a second image 102-2 of a house that is associated with a second class 106-2 for images of houses; and a third image 102-3 of a cat that is associated with a third class 106-3 for images of cats. The associations of the images 102 with the corresponding classes 106 are sometimes known as labels of the training data set 100.

As further shown in FIG. 1, each image 102 may be processed by a convolutional neural network 110 that is organized as a series of convolutional layers 112, each having a set of neurons 114 and one or more convolutional filters 116. In the first convolutional layer 112-1, each neuron 114 may apply a first convolutional filter 116-1 to a region of the image, and may output an activation that indicates whether the pixels in the region corresponds to the first convolutional filter 116-1. The collection of activations produced by the neurons 114 of the first convolutional layer 112-1, known as a feature map 118-1, may be received as input by a second convolutional layer 112-2 in the sequence of convolutional layers 112 of the convolutional neural network 110, and the neurons 114 of the second convolutional layer 112-2 may apply a second convolutional filter 116-2 to the feature map 118-1 produced by the first convolutional layer 112-1 to produce a second feature map 118-2. Similarly, the second feature map 118-2 may be received as input by a third convolutional layer 112-3, and the neurons 114 of the third convolutional layer 112-3 may apply a third convolutional filter 116-3 to the feature map 118-2 produced by the second convolutional layer 112-2 to produce a third feature map 118-3. Such machine learning models that include a significant plurality of layers or more complex architectures of layers are sometimes referred to as deep learning models.

As further shown in FIG. 1, the third feature map 118-3 produced by the third and final convolutional layer 112-3 may be received by a classification layer 120, such as a "dense" or fully-connected layer, which may perform a classification of the third feature map 118-3 to determine a classification of the content of the image 102-1. For example, each neuron 114 of the classification layer 120 may apply a weight to each activation of the third feature map 118-3. Each neuron 114 outputs an activation that is a sum of the products of each activation of the third feature map and the weight connecting the neuron 114 with the activation. As a result, each neuron 114 outputs an activation that indicates the degree to which the activations included in the third feature map 118-3 match the corresponding weights of the neuron 114. Further, the weights of each neuron 114 are selected based on the activations of third feature maps 118-3 that are produced by the images 102 of one class 106 of the class set 104. That is, each neuron 114 outputs an activation based on a similarity of the third feature map 118-3 for a currently processed image 102-1 to the third feature maps 118-3 that are produced by the convolutional neural network 110 for the images 102 of one class 106 of the class set 104. A comparison of the output of the neurons 114 of the classification layer 120 may permit the convolutional neural network 110 to perform a classification 122 by choosing the class 106-4 with the highest probability of corresponding to the third feature map 118-3. In this manner, the convolutional neural network 110 may perform a classification 122 of the image 102-1 as the class 106 of images 102 that most closely resemble the image 102.

As further shown in FIG. 1, a training process may be applied to train the convolutional neural network 110 to recognize a class set 104 that is represented by a particular set of images 102 of a training data set 100. During the training process, each image 102 of the training data set 100 may be processed by the convolutional neural network 110, resulting in a classification 122 of the image 102. If the classification 122 is incorrect, the convolutional neural network 110 may be updated by adjusting the weights of the neurons 114 of the classification layer 120 and the filters 116 of the convolutional layers 112 such that the classification 122 of the convolutional neural network 110 is closer to the correct classification 122 for the image 102 being processed. Repeatedly training the convolutional neural network 110 on the training data set 100, while incrementally adjusting the convolutional neural network 110 to produce a correct classification 122 for each image 102, may result in convergence of the convolutional neural network 110, wherein the convolutional neural network 110 correctly classifies the images 102 of the training data set 100 within an acceptable range of error. Examples of convolutional neural network architectures include ResNet and Inception.

As discussed with respect to FIG. 1, machine learning models such as convolutional neural networks 110 may be capable of classifying inputs, such as images 102, based on an arrangement of features with respect to one another, such as a characteristic number, orientation, and positioning of recognizable features. For example, a convolutional neural network 110 may classify an image 102 by producing a first feature map 118-1 indicating the detection of certain geometric shapes, such as curves and lines, that occur in various locations within the image 102; a second feature map 118-2 indicating that the geometric shapes are arranged to produce certain higher-level features, such as a set of curves arranged as a circle or a set of lines arranged as a rectangle; and a third feature map 118-3 indicating that the higher-level features are arranged to produce even higher-level features, such as a set of circles arranged as a wheel and a set of rectangles arranged as a door frame. A neuron 114 of the classification layer 120 of the convolutional neural network 110 may determine that the features of the third feature map 118-3 (such as two wheels positioned between two door frames) are arranged in such a manner as to depict the side of a vehicle such as a car. Similar classification 122 may occur by other neurons 114 of the classification layer 120 to classify images 102 as belonging to other classes 106 of the class set 104, such as an arrangement of two eyes, two triangular ears, and a nose that depicts a cat, or an arrangement of windows, a door frame, and a roof that depicts a house. In this manner, machine learning models such as convolutional neural networks may classify inputs (such as images 102) based upon an arrangement of features that correspond to similar arrangements of features as depicted in the inputs (such as images 102) of a training data set 100. Additional details about convolutional neural networks and other machine learning models, including support vector machines, may be found in U.S. Patent Application 62/959,931, which is incorporated by reference as if fully rewritten herein.

B. Distribution-Based Classification

In some machine learning scenarios, a classification of an input (such as an image) may occur based on an arrangement of recognizable features with respect to one another, such as a number, orientation, and/or positioning of recognizable patterns of pixels as detected in a feature map 118 of a convolutional neural network 110. However, in some other scenarios, the classification may not be based on an arrangement of features with respect to one another, but instead based on a distribution of features in the input, such as whether a density variance of a feature over the area of the input correspond to a recognizable density variation that is characteristic of a class 106. That is, the classes 106 of a class set 104 might not be recognizable as a set of lower-level features corresponds to a recognized arrangement (e.g., number, orientation, and/or positioning) of higher-level features with respect to one another that corresponds to a class 106. Instead, each class 106 may be recognizable as a correspondence of the distribution of the activation of a feature with some properties of the input. Such distribution may not reflect any particular number, orientation, and/or positioning of the activations of features of the input, but, rather, may indicate whether the distribution of the activation of the feature corresponds to the distribution of the activation of the feature for respective classes 106. In such scenarios, the inputs of each class 106 (such as a training data set) may be associated with a characteristic distribution of the activation of the feature, and a classification of an input may be based upon whether the distribution of the activation of the feature of the input corresponds to the distribution of the activation of the feature among the inputs of each class 106. Such distribution-based classification may also arise in a variety of scenarios.

Figure 2A:
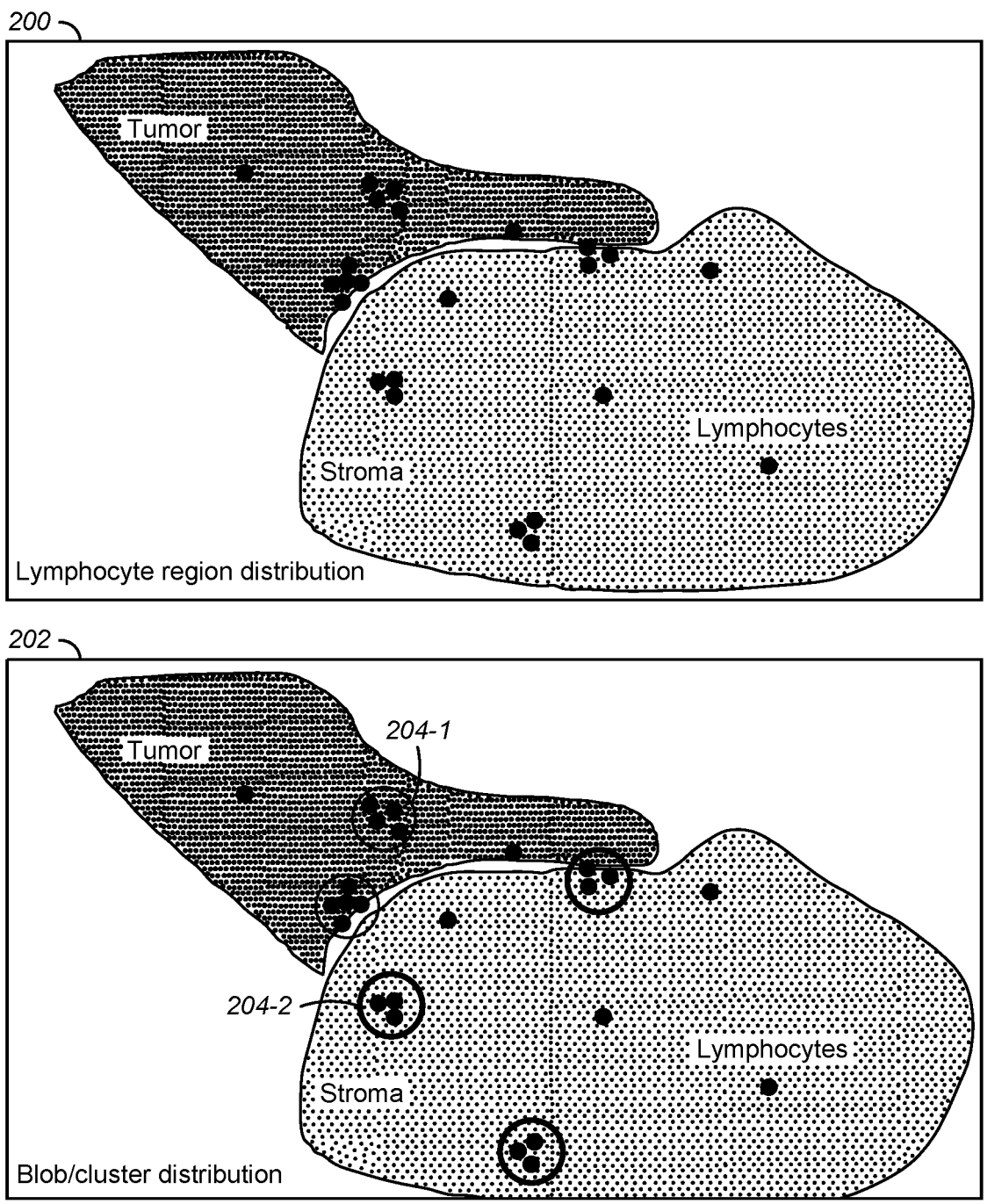
FIG. 2A is an illustration of an example image analysis to identify area types and distributions of lymphocytes in an image of a tumor in accordance with some example embodiments.
Figure 2B:
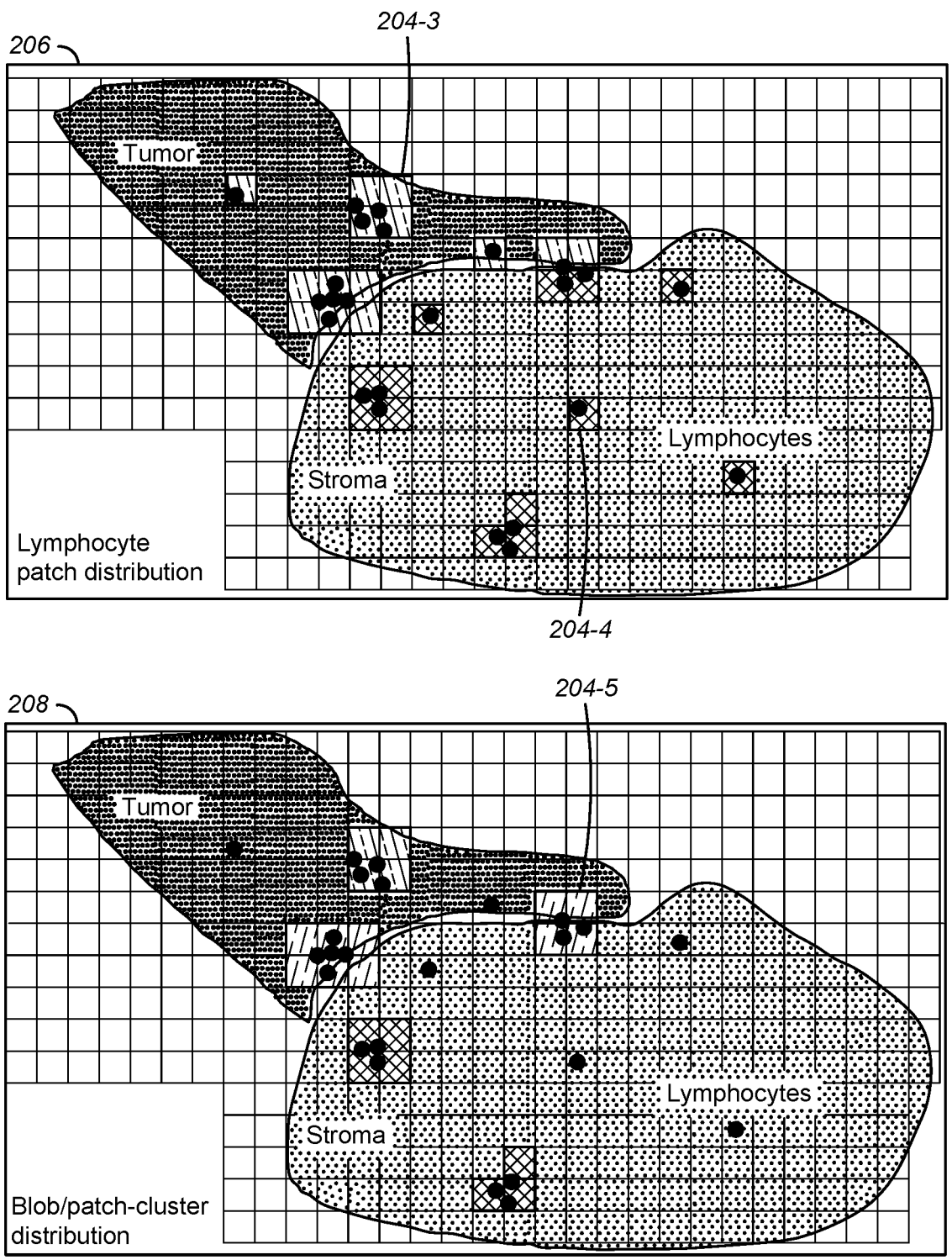
FIG. 2B is an illustration of an example image analysis to classify the distribution of lymphocytes in an image of a tumor in accordance with some example embodiments.

FIGS. 2A and 2B together show an example of several types of image analysis that may be used to identify area types and distributions of lymphocytes in an image of a tumor in some example embodiments.

FIG. 2A is an illustration of an example image analysis to identify area types and distributions of lymphocytes in an image of a tumor in accordance with some example embodiments. As shown in FIG. 2A, a data set may include an image 102 of tissue of an individual with a type of tumor, as well as stroma that includes connective tissue and support for the tumor. Classification of the features of the image 102 may enable a determination of areas, for example, portions of the image 102 that have areas with similar features. A further identification of areas of the feature map 118 that include a certain feature of a filter 116 may enable a determination 200 of area types of the respective areas, such as a first area the image 102 that depicts a tumor, and a second area of the image 102 that depicts stroma. Each filter 116 of the convolutional neural network 110 may therefore be regarded as a mask that indicates the areas of the image 102 of a particular area type, such as the presence, size, shape, and extent of a tumor, or of stroma that is adjacent to a tumor.

Further, the image 102 may show the presence of lymphocytes, which may be distributed with regard to the tumor, stroma, and other tissue. Further analysis of the image may enable a determination 202 of lymphocyte clusters 204 as contiguous areas and/or as areas in which a concentration of lymphocytes is high (for example, compared with the concentration of lymphocytes in other parts of the image, or with a concentration threshold), for example, by counting the number of lymphocytes present within a particular area of the image 102. Thus, the lowest convolutional layers 112 and filters 116 of a convolutional neural network 110 may be capable of identifying features that are indicative of tumor, stroma, and lymphocytes.

FIG. 2B is an illustration of an example image analyses to classify the distribution of lymphocytes in an image of a tumor in accordance with some example embodiments. In FIG. 2B, a first image analysis 206 may be performed by first partitioning the image 102 into a set of areas, and classifying each area of the image 102 as tumor, tumor-adjacent, stroma, stroma-adjacent, or elsewhere. As a result, each area that includes a lymphocyte cluster 204 may further characterize the lymphocyte cluster 204 based on the area type, for example, a first lymphocyte cluster 204-3 that occurs within a tumor and a second lymphocyte cluster 204-4 that occurs within stroma.

A second image analysis 208 may be performed to further compare the locations of lymphocyte clusters 204 with the locations of different area types to further characterize the lymphocyte clusters 204. For example, the first lymphocyte cluster 204-3 may be identified as occurring within a central part of a tumor area, and/or within a first threshold distance of a location identified as a center of mass of the tumor, and may therefore be characterized as a tumor-infiltrating lymphocyte (TIL) cluster. Similarly, the second lymphocyte cluster 204-4 may be identified as occurring within a central part of a stroma area, and therefore representing a stroma-infiltrating lymphocyte cluster. However, a third cluster 204-5 may be identified as occurring within a peripheral part of a tumor area, and/or within a second threshold distance of the tumor (the second threshold distance being larger than the first threshold distance), and may therefore be characterized as a tumor-adjacent lymphocyte cluster. Alternatively or additionally, the third cluster 204-5 may be identified as occurring within a peripheral part of a stroma area, and/or within a second threshold distance of the stroma (the second threshold distance being larger than the first threshold distance), and may therefore be characterized as a stroma-adjacent lymphocyte cluster. Some example embodiments may classify the area as tumor, stroma, or lymphocytes; with two labels, such as tumor and lymphocytes, stroma and lymphocytes, or tumor and stroma; and/or with three labels, such as tumor, stroma, and lymphocytes. Some example embodiments may then be configured to identify clusters 204 of lymphocytes that appear in each area of the image 102, and to tabulate the areas to determine the distribution. In this manner, the image analysis of the image 102, including the feature maps 118 provided by different filters 116 of the convolutional neural network 110, may be used to identify and characterize the distribution and/or concentration of lymphocyte sin the image of the tumor in some example embodiments.

Figure 3:
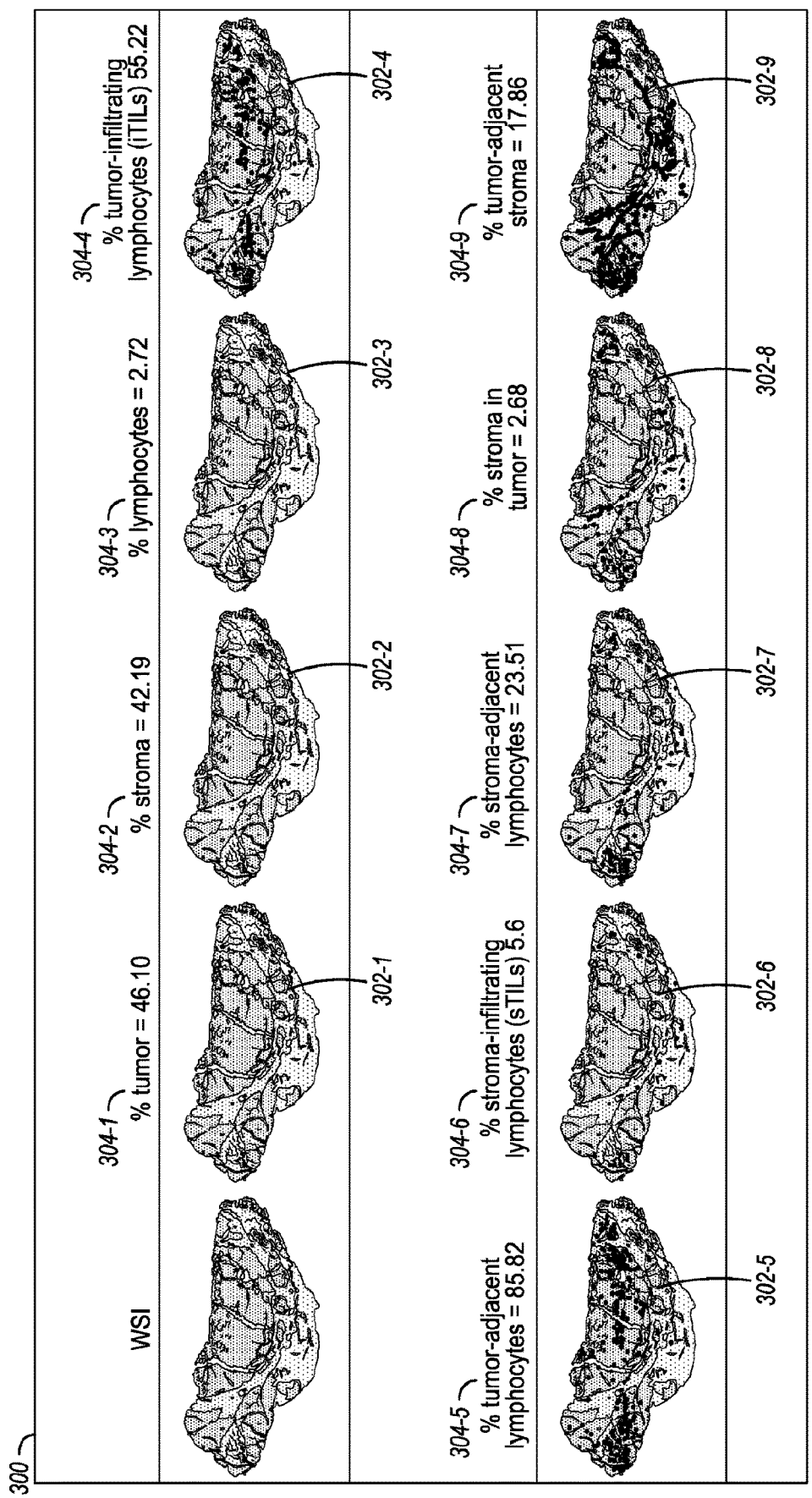
FIG. 3 is an illustration of a set of masks of lung tissue samples including a lymphocyte distribution of lymphocytes by an example machine learning model in accordance with some example embodiments.

FIG. 3 is an illustration of a mask set 300 of masks 302 of lung tissue samples including a lymphocyte distribution of lymphocytes by an example machine learning model in accordance with some example embodiments. As shown in FIG. 3, masks 302 of the image 102 may be prepared, each mask 302 indicating the area of the image 102 that correspond to one or more area types. For example, a first mask 302-1 may indicate areas of the image 102 that are identified as tumor areas. A second mask 302-2 may indicate areas of the image 102 that are identified as stroma areas. A third mask 302-3 may indicate areas of the image 102 that are identified as lymphocyte areas. Still further masks may be characterized based on the distribution of the features in the feature maps 118. For example, a fourth mask 302-4 may indicate areas of the image 102 that are identified as tumor-infiltrating lymphocyte areas. A fifth mask 302-5 may indicate areas of the image 102 that are identified as tumor-adjacent lymphocyte areas. A sixth mask 302-6 may indicate areas of the image 102 that are identified as stroma-infiltrating lymphocytes areas. A seventh mask 302-7 may indicate areas of the image 102 that are identified as stroma-adjacent lymphocytes areas. An eighth mask 302-8 may indicate areas of the image 102 that are identified as overlapping stroma areas and tumor areas. A ninth mask 302-9 may indicate areas of the image 102 that are identified as tumor-adjacent stroma areas.

In some example embodiments, the image 102 may also be processed to determine a variety of measurements 304 of the respective area types of the image 102. For example, a concentration of each area type, as a percentage of the image 102, may be calculated (e.g., the number of pixels 108 corresponding to each area as compared with the total number of pixels of the image 102, optionally taking into account an apparent concentration of the features, such as a density or count of lymphocytes in respective areas of the image 102). In this manner, the image analysis of the image 102 based on the distribution analysis shown in FIGS. 2A and 2B may be aggregated as a mask set 300 of masks 302 and/or quantities in some example embodiments.

Figure 4:
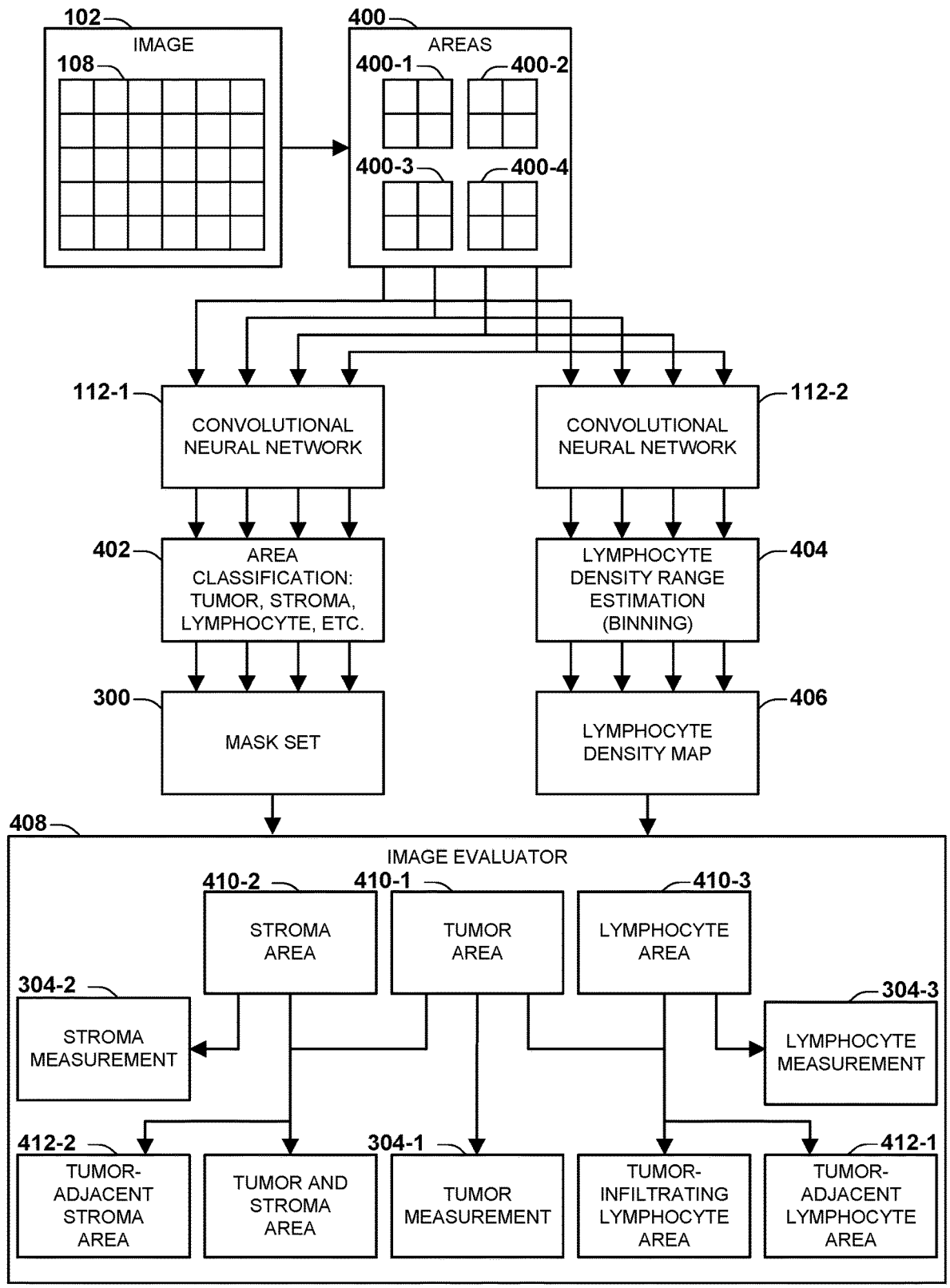
FIG. 4 is an illustration of an example machine learning model that classifies tumors in accordance with some example embodiments.

FIG. 4 is an illustration of an example machine learning model that classifies tumors in accordance with some example embodiments. The example machine learning model of FIG. 4 includes a first convolutional neural network 112-1 configured to perform an area classification 402 of respective areas 400 of an image 102 of a tumor according to different classes, such as tumor areas, stroma areas, lymphocyte areas, tumor-infiltrating lymphocyte areas, etc. Based on the area classification 402, a mask set 300 of masks 302 may be generated, for example, a first mask 302-1 indicating areas 400 of the image 102 that are tumor areas, a second mask 302-2 indicating areas 400 of the image 102 that are stroma areas, and a third mask 302-3 indicating areas 400 of the image 102 that are lymphocyte areas. The example system of FIG. 4 includes a second convolutional neural network 112-2 configured to determine a density or concentration of various features, such as a lymphocyte density range estimation 404 indicating a count or percentage of lymphocytes in respective areas 400 of the image 102. Based on the lymphocyte density range estimation 404, a lymphocyte density map 406 may be generated that indicates the areas 400 of the image 102 having a high density of lymphocytes, such as lymphocyte clusters. Based on the masks 302 of the mask set 300, area classification 402, and/or the lymphocyte density map 406 of the lymphocyte density range estimation 404, an image evaluator 408 may identify aggregated areas of the image 102, such as a tumor area 410-1, a stroma area 410-2, and a lymphocyte area 410-3; one or more measurements of the areas, such as a tumor measurement 304-1, a stroma measurement 304-2, and a lymphocyte measurement 304-3; and/or one or more areas indicating a distribution of the features, such as a tumor-infiltrating lymphocyte area, a tumor-adjacent lymphocyte area 412-1, a tumor and stroma area, and a tumor-adjacent stroma area 412-2.

To recap, in some such example embodiments, one or more convolutional neural networks may be trained to determine a lymphocyte distribution of lymphocytes in an area of an image, for example, to classify an area of the image as one or more area types selected from an area type set including a tumor area, a lymphocyte, area, or a stroma area. In some example embodiments, the convolutional neural network may determine the lymphocyte distribution of lymphocytes in the tumor includes, for respective lymphocyte areas of the image; determine a distance of the lymphocyte area to one or both of a tumor area or a stroma area; and based on the distance, characterize the lymphocyte area as one of, a tumor-infiltrating lymphocyte area, a tumor-adjacent lymphocyte area, a stroma-infiltrating lymphocyte area, or a stroma-adjacent lymphocyte area. In some example embodiments, the convolutional neural network may determine the lymphocyte distribution of lymphocytes in the tumor by, for respective stroma areas of the image, determining a distance of the stroma area to a tumor area, and based on the distance, characterizing the stroma area as one of, a tumor-infiltrating stroma area, or a tumor-adjacent stroma area, and the classifier further classifies the tumor based on the characterizing of the stroma area. The classifier may thus further classify the tumor based on the characterizing of the lymphocyte area. Many such convolutional neural networks may perform a variety of analyses of the image that may inform a determination of a clinical value (such as a prognosis) for an individual in some example embodiments.

C. Learning Parameter Determination

Figure 5:
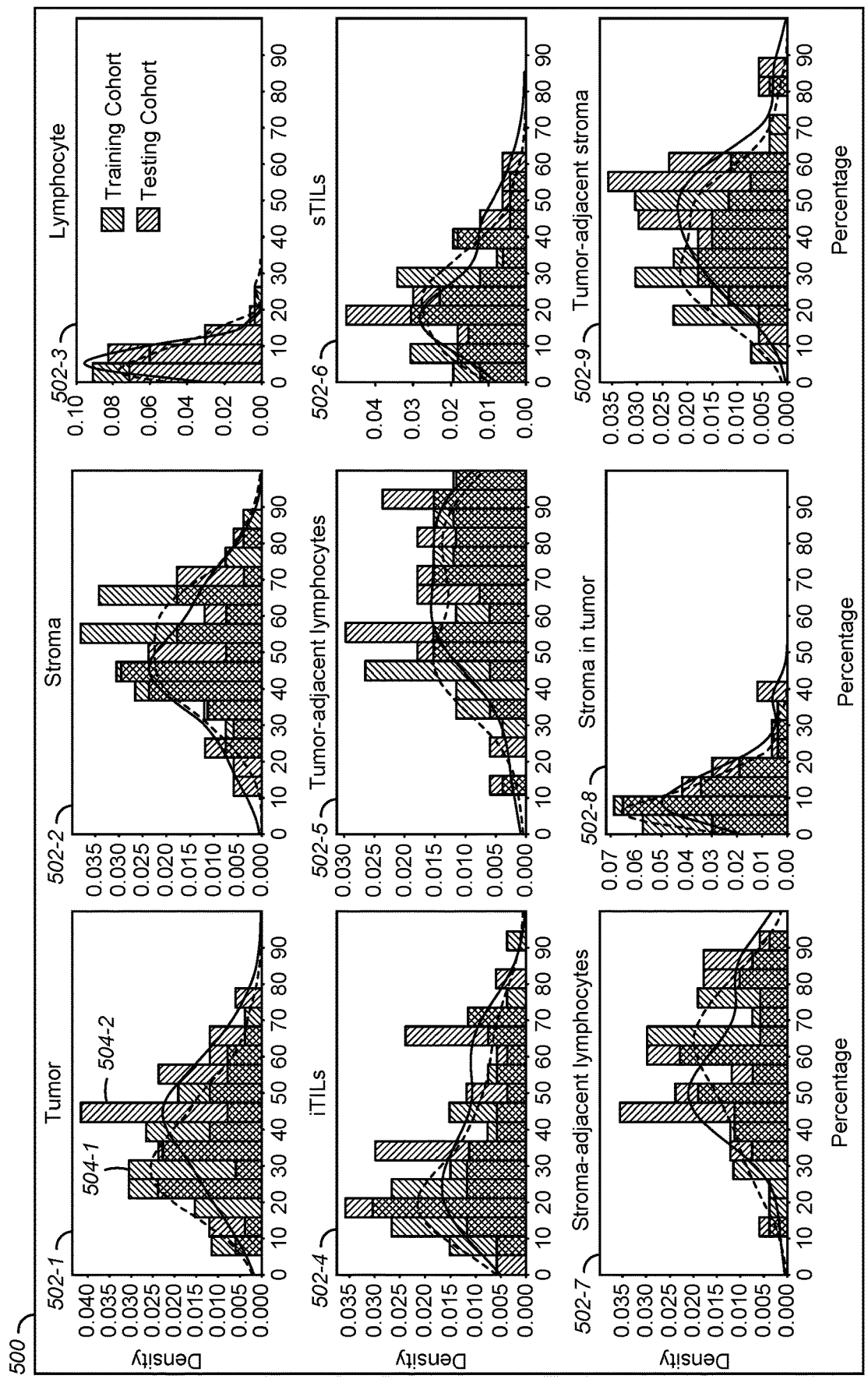
FIG. 5 is an illustration of a characterization of a set of images of pancreatic adenocarcinoma tissue samples in accordance with some example embodiments.

FIG. 5 is an illustration of a characterization 500 of a set of images of pancreatic adenocarcinoma tissue samples in accordance with some example embodiments. In the charts of FIG. 5, a set of tumors is characterized by the system shown in FIG. 4 to determine a distribution of the detected features of tumor, such as tumor areas 502-1, stroma areas 502-2, lymphocyte areas 502-3, tumor-invasive lymphocyte areas 502-4, tumor-adjacent lymphocyte areas 502-5, stroma- and tumor-invasive lymphocyte areas 502-6, stroma-adjacent lymphocyte areas 502-7, tumor and stroma areas 502-8, and tumor-adjacent stroma areas 502-9. Each feature may be evaluated as to both a density or concentration (vertical axis) and a percentage (horizontal axis) of each feature in the images 102 of the tumors. The set of images of tumors may be further divided into a subset of training images, which may be used to train a machine learning classifier such as the neural networks 112-1, 112-2 to determine the features, and a subset of testing images, which may be used to evaluate the effectiveness of the machine learning classifiers in determining the features in previously unseen images of tumors. In this manner, the machine learning classifier may be validated to determine the consistency of the underlying logic when applied to new data. For example, the chart in FIG. 5 was developed based on diagnostic hematoxylin and eosin stain (H&E-stain) of pathology images of pancreatic adenocarcinoma patients who underwent chemotherapy.

It may be further desirable to characterize the tumors as one of several classes, such as low-risk tumors and high-risk tumors, on the basis of factors that are characteristic of tumors of each class. For example, tumors of respective classes may also be associated with different features, such as concentration and/or percentage of a particular type of tumor area (e.g., tumor-invasive lymphocytes), and differences in such characteristic features may enable the tumors of one class to be distinguished from tumors of another class. Further, different tumor classes may be associated with different clinical properties, such as responsiveness to various treatment options and prognosis such as survivability. In order to determine such clinical properties for a particular tumor in an individual, it may be desirable to determine the tumor class of the tumor in order to guide the selection of a diagnosis and/or treatment regimen for the individual.

However, in many diagnostic scenarios, it may be difficult to associate the features that are characteristic of the different classes, such as different tumor classes. As a first such example, the features of tumors in one class may vary from the features of tumors in another class within a probabilistic range, and the probabilistic ranges may overlap by a significant amount. For example, the characteristic density and percentages of tumor-invasive lymphocytes for a high-risk tumor class and a low-risk tumor may each fit a bell curve of probability within the tumor class, and the means of the bell curves being only marginally offset, such that the probabilistic distributions may overlap. It may therefore be difficult to determine whether a tumor exhibiting the feature within the overlapping areas is of the high-risk class or the low-risk class. As a second such example, different features of tumors may covary; for example, high-risk tumors may be distinguished from low-risk tumors based on the combined probabilities of distinguishing distributions of tumor-invasive lymphocyte areas and tumor-adjacent lymphocyte areas. However, different features may also innately covary in ways that are not diagnostic. For example, tumors that exhibit a high density of stroma- and tumor-invasive lymphocyte areas also necessarily exhibit a high density of tumor-invasive lymphocyte areas in general. As a result, adding the class-based probability of a tumor belonging to a class on the basis of stroma- and tumor-invasive lymphocyte areas and the class-based probability of a tumor belonging to a class on the basis of tumor-invasive lymphocyte areas may overweigh the likelihood of a tumor being in the class, due to failing to account for the innate covariance of the features. Due to these complex features of the data, it may be difficult to determine the distinguishing features for each class of tumors, particularly in high-dimensionality feature sets where many features may be available.

In order to classify a data set that exhibits such overlapping classes of data, a variety of machine learning models may be used. Respective machine learning models may provide different capabilities of classifying the overlapping data sets, for example, on the basis of distinctiveness, tolerance for false positives, tolerance for false negatives, scalability to larger numbers of features, and avoidance of properties such as overfitting and underfitting.

Figure 6A:
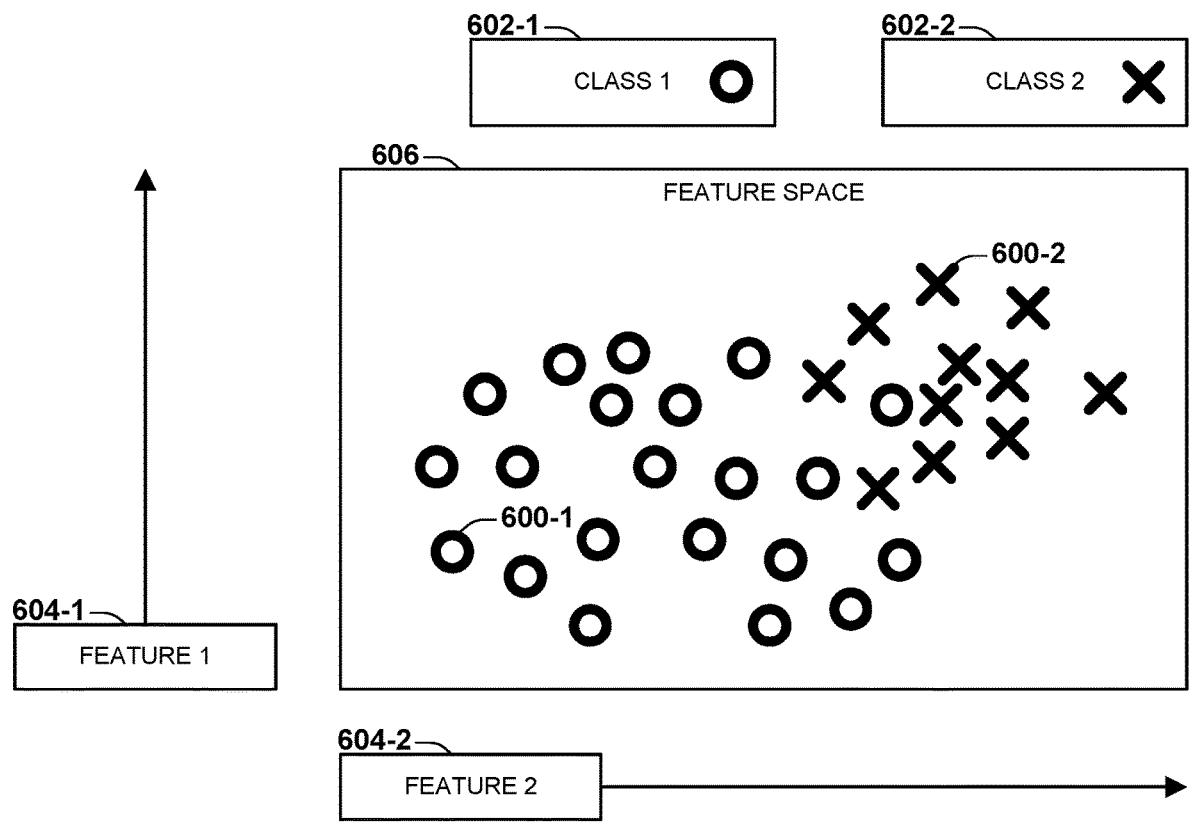
FIG. 6A is an illustration of a set of samples arranged in a two-dimensional feature space.
Figure 6B:
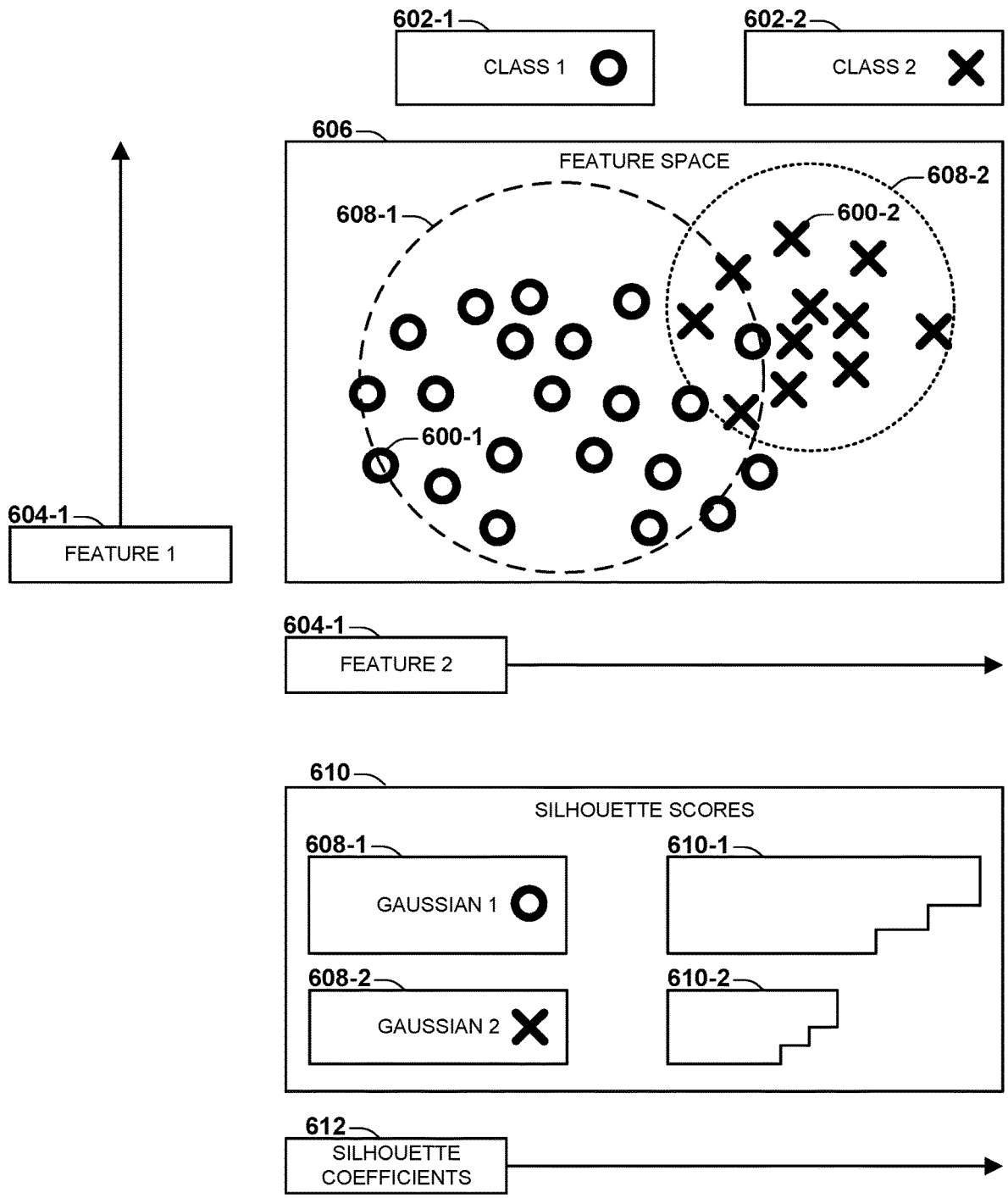
FIG. 6B is an illustration of a Gaussian mixture model configured to classify the set of samples into a set of clusters of probability distributions within the two-dimensional feature space.
Figure 6C:
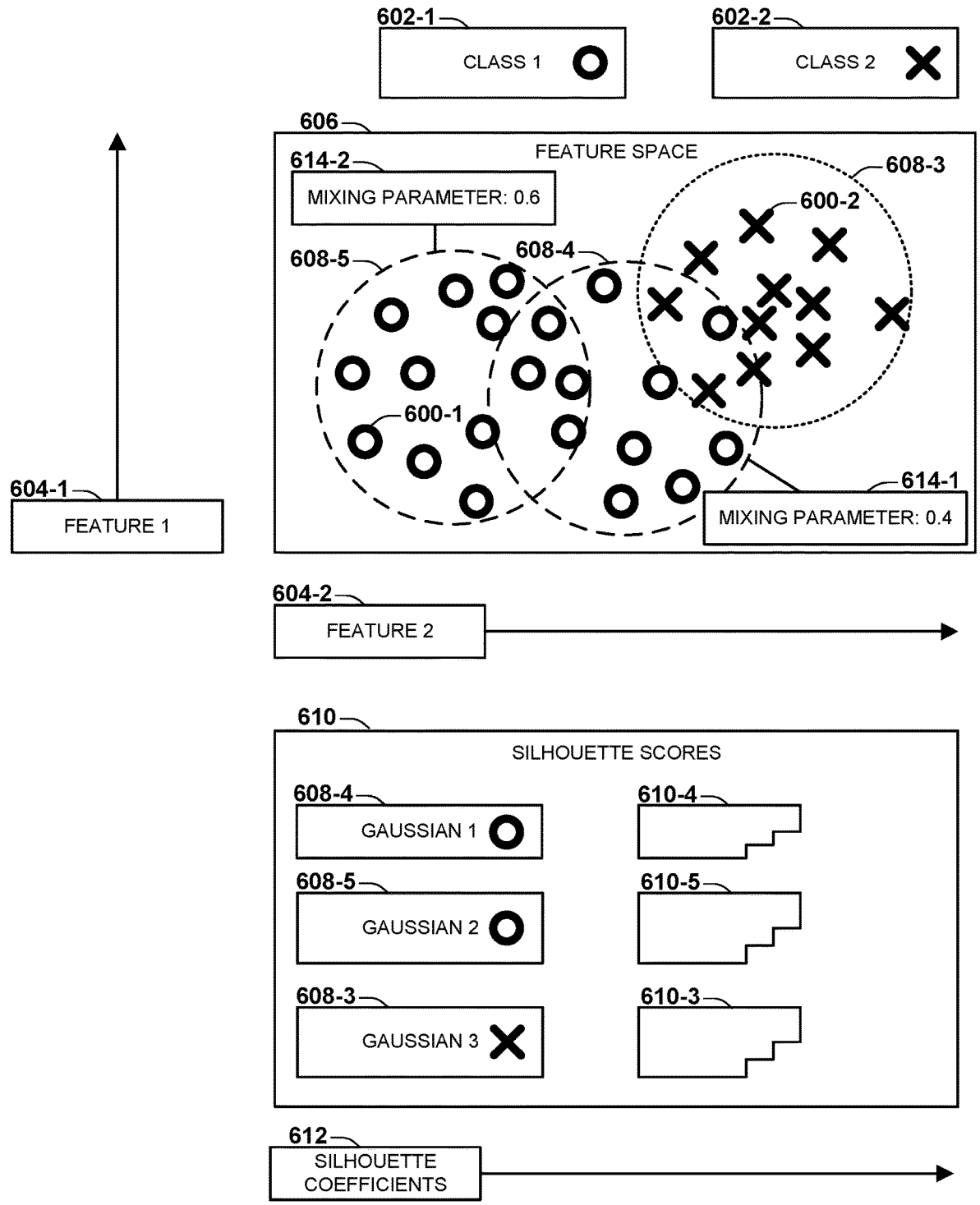
FIG. 6C is another illustration of a Gaussian mixture model configured to classify the set of samples into a set of clusters of probability distributions within the two-dimensional feature space.

FIGS. 6A-6C together show an example of a Gaussian mixture model that may be developed to classify overlapping classes of data, such as classifying tumors into low-risk tumors and high-risk tumors on the basis of two features, which may be used in some example embodiments.

FIG. 6A is an illustration of a set of samples arranged in a two-dimensional feature space 606. In FIG. 6A, the feature space 606 involve samples 600-1 of a first class 602-1 (represented as circles) and samples 600-2 of a second class 602-2 (represented as crosses). Each sample 600 may be evaluated and quantified as to a first feature 604-1 and a second feature 604-2, which may enable each sample to be positioned within the two-dimensional feature space 606, wherein the vertical axis represents the first feature 604-1 and the horizontal axis represents the second feature 604-2. Within the two-dimensional feature space 606, the samples 600 of each class 602 may be apparently clustered, but the clusters may also overlap, such that samples within the overlapping part may belong to either class 602. For a particular sample 600, it may be desirable to determine a probability that the sample 600 belongs in each class 602 based upon the features 604 of the sample 600, particularly in the overlapping area that is associated with samples 600 of multiple classes 602. While the clustering may be apparent in the simple illustration of FIG. 6A, such clustering may be more difficult to determine, for example, in feature spaces 606 with higher dimensionality, in data sets featuring classes 602 with a greater degree of overlap, and/or in data sets in which two or more features 604 covary for which determining the diagnostic or innate covariance of the features 604.

A variety of machine learning models may be used to classify overlapping data sets, such as shown in FIG. 6A. Some such models include, for example, Bayesian (including naïve Bayesian) classifiers; Gaussian classifiers; probabilistic classifiers; principal component analysis (PCA) classifiers; linear discriminant analysis (LDA) classifiers; quadratic discriminant analysis (QDA) classifiers; single-layer or multiplayer perceptron networks; convolutional neural networks; recurrent neural networks; nearest-neighbor classifiers; linear SVM classifiers; radial-basis-function kernel (RBF) SVM classifiers; Gaussian process classifiers;

decision tree classifiers, including random forest classifiers; and/or restricted or unrestricted Boltzmann machines, among others FIG. 6B is an illustration of a Gaussian mixture model configured to classify the set of samples 600 shown in FIG. 6A into a set of clusters of probability distributions within the two-dimensional feature space 606, and which may be used to distinguish different classes of tumors in some example embodiments. In FIG. 6B, a first Gaussian probability distribution 608-1 may be identified for the samples 600-1 of the first class 602-1, and a second Gaussian probability distribution 608-2 may be identified for the samples 600-2 of the second class 602-2. The Gaussian probability distributions 608 for each class 602 may be fit to the samples 600 of each class 602, for example, based on the mean and variance of the samples 600 for each feature 604. The selection of the Gaussian probability distributions 608 may also take into consideration other factors such as avoiding false negatives (e.g., samples 600 of the class 602 being incorrectly excluded from the class 602) and/or avoiding false positives (e.g., samples 600 of a different class 602 being incorrectly included in the class 602). Further, the Gaussian probability distributions 608 may be selected to model covariance, for example, by associating the distribution of the Gaussian probability distribution 608 for the first feature 604-1 and the distribution of the Gaussian probability distribution 608 for the second feature 604-2. For example, a similar deviation and/or of the Gaussian probability distribution 608 may be selected for the first feature 604-1 and the second feature 604-2, or may be independently selected for each feature 604. For a particular sample 600 (such as an image of a tumor of an unknown class), the features 604 of the sample 600 may be evaluated to position the sample 600 within the feature space 606, and the relative probabilities within the Gaussian probability distributions 608 of the respective classes 602 may be compared to determine a likely class 602 of the tumor.

As further shown in FIG. 6B, the fitness of the selected Gaussian mixture model may also be evaluated, for example, as an estimate of the diagnostic properties of the Gaussian mixture model. For example, a silhouette score 610 may be determined for each Gaussian probability distribution 608, where the silhouette score indicates a silhouette coefficient 612 (e.g., the number of samples 600 of the class 602 that are within a selected distance from the mean or center of mass of the Gaussian probability distribution 608). The distinguishing properties of the Gaussian mixture model may be improved by selecting Gaussian probability distributions 608 with similar silhouette scores 610. As shown in FIG. 6B, the silhouette scores of the Gaussian probability distributions 608 are dissimilar, for example, because the first Gaussian probability distribution 608-1 for the first class 602-1 represents a larger number of samples 600-1 than the second Gaussian probability distribution 608-2 for the samples 600-2 of the second class 602-2 (that is, a taller silhouette for the first Gaussian probability distribution 608-1 than for the second Gaussian probability distribution 608-2), and also because the distances of the samples 600-1 of the first class 602-1 are more widely distributed in the feature space 606 than the samples 600-2 of the second class 602-2, leading to a larger range of silhouette coefficients 612 (that is, a longer silhouette for the first Gaussian probability distribution 608-1 than for the second Gaussian probability distribution 608-2). As a result, the Gaussian mixture model of FIG. 6B may be improved by selecting a different mixture of Gaussian probability distributions 608.

FIG. 6C is another illustration of a Gaussian mixture model configured to classify the set of samples into a set of clusters of probability distributions within the two-dimensional feature space, and which may be used to distinguish different classes of tumors in some example embodiments. In FIG. 6C, the Gaussian probability distributions for the first class 602 are instead identified as a first Gaussian probability distribution 608-4 for a first cluster of samples 600-1 of the first class 602-1 and a second Gaussian probability distribution 608-5 for a second cluster of samples 600-1 of the first class 602-1. Further, for each of the Gaussian probability distributions 608, a mixing parameter may be identified that indicates the proportion of samples 600 of the class 602 that are represented by the Gaussian probability distribution 608. For example, the first Gaussian probability distribution 608-4 for the first class 602-1 may fit a smaller number of samples 600-1 of the first class 602-1 than the second Gaussian probability distribution 608-5 for the first class 602-1, and may therefore have a smaller first mixing parameter 614-1 than a second mixing parameter 614-2 for the second Gaussian probability distribution 608-5. When a sample 600 of an unknown class 602 is positioned within the feature space 606, the probability of the sample 600 being classified into each class 602 may be determined as the sum of the products of the probability distributions for the position of the sample 600 by each Gaussian probability distribution 608 and the mixing parameter 614 for the Gaussian probability distribution 608. Further, the classifying capability of the Gaussian mixture model may be evaluated based on the silhouette scores 610 of the respective Gaussian probability distributions 608; for example, the similarities of both sample size and silhouette coefficients 612 for each Gaussian probability distribution 608, may indicate a more reliable and predictive classifier than the Gaussian mixture model of FIG. 6B.

Alternatively or in addition to the silhouette scores shown in FIGS. 6B and 6C, other measures may be used to determine the classifying capabilities of a Gaussian mixture model. As one example, for tumors of different tumor classes (such as a low-risk class and a high-risk class) that are respectively associated with survivability, a concordance index ("C-index") may be developed that indicates a degree of consistency between a predicted survival time of individuals with tumors of a tumor class and the actual survival times of individuals with tumors of the tumor class. Concordance indices may be determined on the basis of each feature of the tumor class to determine the degree to which the feature corresponds to the predicted survival rate of the individuals with tumors in the tumor class, where a high concordance index indicates a highly predictive feature of the Gaussian mixture model and a low concordance index indicates a poorly predictive feature of the Gaussian mixture model. Because the concordance index of each feature depends upon the selected Gaussian mixture model, it may be desirable to limit the number of features to those that exhibit a high concordance index, alternatively or additionally to the silhouette scores of the respective Gaussian probability distributions for each class. Selecting such features may reduce the dimensionality of the feature space 606 of the data set to a smaller set of features that are more highly distinguishing for the respective classes 602, which may yield a more precise, accurate, and/or efficient classification process.

FIG. 7 is an illustration of a selection process 700 for selecting a clinical feature subset for a classifier from a clinical feature set of clinical features within a feature space based on a correlation of respective clinical features with respective classes in accordance with some example embodiments. A Gaussian mixture model is developed for a set of nine clinical features, such as the nine clinical features shown in FIG. 5. A set of silhouette scores and concordance indices may be determined for each clinical feature. Among a set of available clinical features 704, in a first selection step 702-1, a first clinical feature 706-1 may be selected that provides with a highest silhouette score and/or concordance index among the available clinical features 704, such a concentration (specifically, percentage) of tumor-adjacent lymphocyte areas. Among the remaining clinical features (that is, all of the clinical features except the first selected clinical feature), in a second selection step 702-2, a second Gaussian mixture model may be developed, and a second clinical feature 706-2 may be selected that provides with a highest silhouette score and/or concordance index among the remaining clinical features, such a concentration (specifically, percentage) of stroma and tumor areas. Similar selection steps 702-3, 702-4 may be performed to select a third clinical feature 706-3 (such as concentration of tumor-invasive stroma areas) and a fourth clinical feature 706-4 (such as concentration of lymphocytes), each of which provides an improved concordance score as compared with the previously selected clinical features, indicating a supplemental classification capability of the selected clinical feature as compared with the other remaining clinical features. The selection process may continue until a fifth selection step 702-5, in which the selected clinical feature is determined not to improve upon the concordance indices of the previously selected clinical features, and no further clinical features may be selected for the clinical feature subset.

To recap, in some example embodiments, a classifier for a tumor may include Gaussian mixture model configured to determine, for respective classes, a probability distribution of features for tumors in the class within a feature space, which may be selected from a feature set including a measurement of tumor areas of the image, a measurement of stroma areas of the image, a measurement of lymphocyte areas of the image, a measurement of tumor-infiltrating lymphocyte areas of the image, a measurement of tumor-adjacent lymphocyte areas of the image, a measurement of stroma-infiltrating lymphocyte areas of the image, a measurement of stroma-adjacent lymphocyte areas of the image, a measurement of tumor-infiltrating stroma areas of the image, and a measurement of tumor-adjacent stroma areas of the image. In some example embodiments, a feature subset for the Gaussian mixture model may be selected based on a correlation of the respective classes with respective features of the subset, wherein the correlation may be based on one or both of, a silhouette score of the feature space or a concordance index. In some example embodiments, the feature subset may consist essentially of the measurement of lymphocyte areas of the image, the measurement of tumor-infiltrating lymphocyte areas of the image, the measurement of tumor-adjacent lymphocyte areas of the image, and the measurement of tumor-infiltrating stroma areas of the image.

D. Image-Based Tumor Evaluation

In some example embodiments, a clinical value (such as a prognosis) for an individual based on a tumor shown in an image may be determined by determining a lymphocyte distribution of lymphocytes in the tumor based on the image; applying a classifier to the lymphocyte distribution to classify the tumor, the classifier having been trained to classify tumors into a class selected from at least two classes respectively associated with lymphocyte distributions; and determining the clinical value (such as the prognosis) for the individual based on prognoses of individuals with tumors in the class into which the classifier classified the tumor. The classifier may be invoked to determine the lymphocyte distribution of lymphocytes in respective areas of the image of the tumor.

FIG. 8 is an illustration of a classification of tumors of different classes based on a feature subset in accordance with some example embodiments. FIG. 8 presents a comparison 800 of the feature subset of selected features 806 with the images 804 of tumors of a low-risk tumor class 802-1 and a high-risk tumor class 802-2, that is, in the percentages of areas in each image 804 of each class 802 corresponding to each of the features 806 of the feature subset. The high-risk class of tumors may be associated with a first survival probability, and the low-risk class of tumors may be associated with a second survival probability that is longer than the first survival probability. The percentages of the respective features 806 of the images 804 of the tumor classes 802 may be compared, for example, to determine the degree to which the features 806 are diagnostic of the respective tumor classes 802. For example, the images 804 of the high-risk tumor class 802-2 may demonstrate a smaller and more consistent range of values for the first feature 806-1 and the third feature 806-2 than for the images 804 of the low-risk tumor class 802-1. Also, the values for the third feature 806-3 may be typically higher in images of tumors of the low-risk tumor class 802-1 than in images of tumors of the high-risk tumor class 802-2. These measurements, which may be determined based on selected features 706 of the feature subsets of the tumor classes 802 based on the selection process 700 of FIG. 7, may present clinically significant findings in the pathology of tumors of different tumor classes 802, and may be used by both clinicians and automated processes (such as diagnostic and/or prognostic machine learning processes) to classify tumors into different tumor classes 802.

Figure 9:
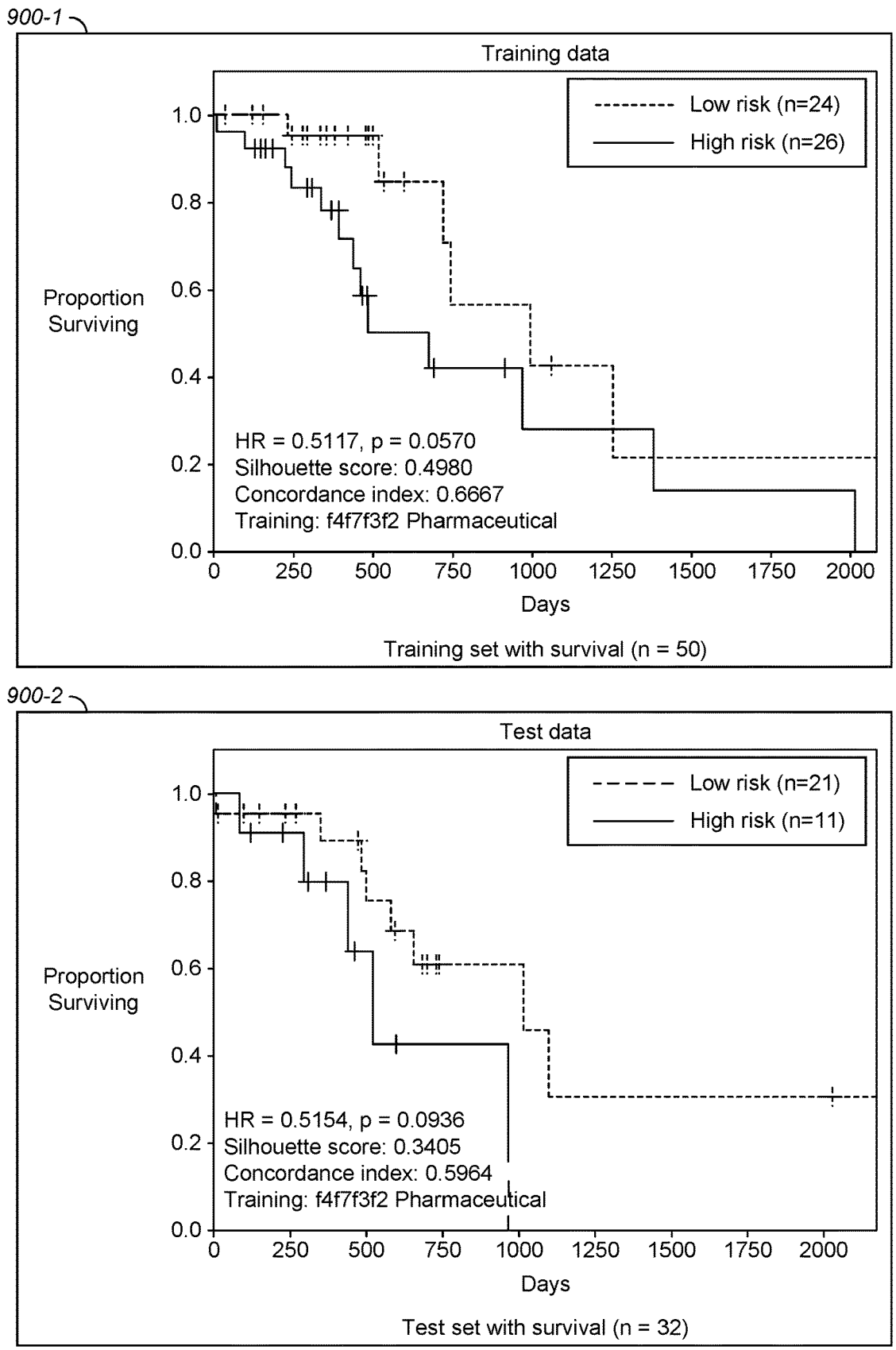
FIG. 9 is an illustration of a Kaplan Meier survivability plot based on image analysis in accordance with some example embodiments.

FIG. 9 is an illustration of a Kaplan Meier survivability plot based on image analysis in accordance with some example embodiments. In FIG. 9, a first Kaplan Meier survivability plot 900-1 and a second Kaplan Meier survivability plot 900-2 (e.g., percentages of surviving populations of individuals as measured by days after diagnosis) are generated, respectively, for a training set and test set based on a population of individuals having tumors of the low-risk tumor class 802-1 and the high-risk tumor class 802-2 of FIG. 8. Further, the set of tumors for which images and data are available is separated into a training set and a test set. The machine learning models, including the convolutional neural networks and/or the Gaussian mixture models, are trained on the images of the training set to a convergence point in which the machine learning models produce output that is within an accuracy range of the expected output. The machine learning models are then tested using the test set to determine whether the machine learning models produce output for new data that is consistent with the expected output. Such validation may include cross-validation processes in which the set of tumors is first partitioned into a number of subsets, and repeated training and testing are performed using a selection from the subsets for the training set and the remaining subsets for the test set.

As shown in FIG. 9, the image-based tumor evaluation technique presented herein performed classification on the training data set with a hazard ratio (HR) of 0.5117, a statistical P-value of 0.0570, and a concordance index of 0.6667, and demonstrated performance on the test set with a hazard ratio of 0.5154, a statistical P-value of 0.3405, and a concordance index of 0.5964. Many such machine learning models may be trained to classify tumors and to determine the clinical value (such as the prognosis and/or the survivability) for the individual in accordance with some example embodiments.

E. Cox Proportional Hazards Model

In some example embodiments, the image-based prognosis determination techniques may be combined with a Cox proportional hazards model, which may improve the prognostic capabilities of tumor analysis. The Cox proportional hazards model is a regression model that correlates clinical features, such as the individual's demographic features, clinical observations of the individual and the tumor, and pathology measurements, with different tumor classes to determine the contribution of each clinical feature to the tumor classification. For example, the regression model may determine that individuals within a particular age range, with particular personal habits such as smoking or alcohol usage, and with a cancer staging score, such as based on the American Joint Committee on Cancer (AJCC) cancer staging system, are more likely to be classified with tumors within a low-risk tumor class, while individuals within another age range, having other personal habits, and with other cancer staging scores are more likely to be classified with tumors within a high-risk tumor class.

A Cox proportional hazards model may be developed using a training set featuring tumors with known clinical features. A stepwise selection may be performed to select a subset of clinical features that significantly contribute to classification, for example, by removing the clinical features that do not significantly improve the predictiveness of the other clinical features. The Cox proportional hazards model may also be trained on the tumors of two or more classes to determine different proportional survivability rates for tumors of different tumor classes, such as a low-risk class of tumors having a shared set of properties and/or similar survivability metrics and a high-risk class of tumors having another shared set of properties and/or other similar survivability metrics.

FIG. 10 is an illustration of a selection of a feature subset for a Cox proportional hazards model from a feature set 1000 of features within a feature space based on a correlation of respective features with respective classes in accordance with some example embodiments. In FIG. 10, for respective tumors of a set of tumors taken from individuals and pathologically evaluated, the values for the clinical feature set 1000 are identified that includes a primary diagnosis of the tumor (e.g., a T-category AJCC staging score); a measurement of the tumor (e.g., an N-category AJCC staging score); an ethnicity of the individual; a treatment of the tumor; a location of the tumor; a smoking habit frequency of the individual; a metastatic condition of the tumor; a race of the individual; a previous cancer medical history of the individual; a smoking habit duration of the individual; a primary diagnosis of the individual; an alcohol history of the individual; and a gender of the individual. A first step 1002-1 of regression analysis may determine the extent to which each feature of the feature set 1000 distinguishes between the tumor classes (e.g., low-risk and high-risk), and the features may be ordered, for example, by statistical P-values. The features having P-values within a certain range (for example, below a statistical significance threshold of 0.05) may be selected as a feature subset, and the other features may be excluded. Additional steps 1002-2, 1002-3, 1004 of regression analysis may be performed to exclude other features, and to retain other features of the feature set 1000, until features can no longer be excluded without significantly reducing the classification accuracy of the Cox proportional hazards model. The resulting feature set 1004, based on the correlation of the respective classes with respective features of the subset, may be identified as the retained features of the Cox proportional hazards model.

As shown in FIG. 10, a Cox proportional hazards model developed in this manner identified a feature subset consisting of the measurement of the tumor and the metastatic condition of the tumor. For a training set, the Cox proportional hazards model demonstrated a hazard ratio of 0.2182 and a statistical P-value of 0.0200, and for a test set, the Cox proportional hazards model demonstrated a hazard ratio of 0.4065 and a statistical P-value of 0.2855. Many such Cox proportional hazard models may be determined to classify tumors in accordance with some example embodiments.

F. Combined Model

In some example embodiments, image-based classification (e.g., based on a convolutional neural network and a Gaussian mixture model) may be combined with a Cox proportional hazards model to classify the tumor based on both image features and clinical features. That is, the at least two classes are a low-risk tumor class and a high-risk tumor class; determining the lymphocyte distribution may further include applying a convolutional neural network to the image, the convolutional neural network configured to measure the lymphocyte distribution of lymphocytes for different area types of the image; the classifier may be a two-way Gaussian mixture model configured to determine, for respective classes, a probability distribution of features for tumors in the class within a feature space; a Cox proportional hazards model may be applied to clinical features of the tumor to determine a class of the tumor; and determining the clinical value (such as the prognosis) for the individual may be further based on the class determined by the Cox proportional hazards model.

FIG. 11 is an illustration of a Kaplan Meier survivability plot based on image analysis and a Cox proportional hazards model in accordance with some example embodiments. In FIG. 11, a first Kaplan Meier survivability plot 900-3 and a second Kaplan Meier survivability plot 900-4 (e.g., percentages of surviving populations of individuals as measured by days after diagnosis) are generated, respectively, for a training set and test set based on a population of individuals having tumors of the low-risk tumor class 802-1 and high-risk tumor class 802-2 of FIG. 8. Further, the set of tumors for which images and data, including clinical features, are available is separated into a training set and a test set. The machine learning models, including the convolutional neural networks, the Gaussian mixture models, and the Cox proportional hazards model, are trained on the images of the training set to a convergence point in which the machine learning models produce output that is within an accuracy range of the expected output. The machine learning models are then tested using the test set to determine whether the machine learning models produce output for new data that is consistent with the expected output. Such validation may include cross-validation processes in which the set of tumors is first partitioned into a number of subsets, and repeated training and testing are performed using a selection from the subsets for the training set and the remaining subsets for the test set.

As shown in FIG. 11, the image-based tumor evaluation technique presented herein performed classification on the training data set with a hazard ratio (HR) of 0.2545, a statistical P-value of 0.0065, and a concordance index of 0.7141, and demonstrated performance on the test set with a hazard ratio of 0.3742, a statistical P-value of 0.0696, and a concordance index of 0.6120.

FIG. 12 is an illustration 1200 of a result set of a classification of a tumor training data set and a tumor test data set based on an image analysis and a Cox proportional hazards model in accordance with some example embodiments. As shown in FIG. 12, classification results for the combined model featuring both image-based analysis and statistical analysis of clinical features demonstrate greater classification accuracy than for either model used alone. Many such machine learning models may be trained to classify tumors and to determine the clinical value (such as the prognosis and/or survivability) for the individual in accordance with some example embodiments.

G. Tumor Evaluation and Output

In some example embodiments, the tumor analysis models disclosed herein may be used to determine and output, for a user, a clinical value for an individual based on a tumor shown in an image. The user may be, for example, the individual with the tumor; a family member or guardian of the individual; or a healthcare provider, including a physician, nurse, or clinical pathologist. The clinical value and/or the output may be, for example, one or more of: a diagnosis for the individual, a prognosis for the individual, a survivability of the individual, a classification of the tumor, a diagnostic and/or treatment recommendation for the individual, or the like.

Some example embodiments may use the determination of the tumor analysis model to display a visualization of the clinical value (such as the prognosis) for the individual. For example, a terminal may accept an image of a tumor of an individual, and, optionally, a set of clinical features, such as the individual's demographic features, clinical observations of the individual and the tumor, and pathology measurements. The terminal may apply the tumor analysis model (e.g., processing the image by a convolutional neural network and a Gaussian mixture model, and, optionally, processing the clinical features by a Cox proportional hazards model) to determine a class of the tumor, such as a low-risk tumor class and a high-risk tumor class, and a prognosis that is associated with individuals with tumors of the tumor class. The clinical value may be determined, for example, as a survivability, such as projected survival durations and probabilities, optionally including a confidence or accuracy of each probability. In some example embodiments, the clinical value may be presented as a visualization, such as a Kaplan Meier survivability projection of the tumor. In some example embodiments, the visualization may include additional information about the tumor, such as one or more of the masks 302 that indicate the area types of the areas of the image 102; measurements 304 of the image 102, such as a concentration for each area type (e.g., a concentration of lymphocytes in one re more areas as determined by binning), and/or a percentage area of the area type as compared with the entire image 102. In some example embodiments, the visualization may include additional information about the individual, such as the individual's clinical features, and may indicate how respective clinical features contribute to the determination of the clinical value (such as the prognosis) for the individual.

Some example embodiments may use the determination of the tumor analysis model to determine, and to display for a user, a diagnostic test for the tumor based on the clinical value (such as the prognosis) for the individual. For example, based on the tumor being classified as a low-risk class by the tumor analysis model, an apparatus may recommend less aggressive testing to further characterize the tumor, such as blood tests or imaging. Based on the tumor being classified as a high-risk class by the tumor analysis model, an apparatus may recommend more aggressive testing to further characterize the tumor, such as a biopsy. Some example embodiments may also display, for the user, an explanation of the basis of the determination; a set of options for further testing; and/or a recommendation of one or more options to be considered by the individual and/or a healthcare provider.

Some example embodiments may use the determination of the tumor analysis model to determine, and to display for a user, a treatment of the individual based on the clinical value (such as the prognosis) for the individual. For example, based on the tumor being classified as a low-risk class by the tumor analysis model, an apparatus may recommend less aggressive treatment of the tumor, such as less aggressive chemotherapy. Based on the tumor being classified as a high-risk class by the tumor analysis model, an apparatus may recommend more aggressive treatment of the tumor, such as more aggressive chemotherapy and/or surgical removal. Some example embodiments may also display, for the user, an explanation of the basis of the determination; a set of options for further testing; and/or a recommendation of one or more options to be considered by the individual and/or a healthcare provider.

Some example embodiments may use the determination of the tumor analysis model to determine, and to display for a user, a schedule of a therapeutic agent for treating the tumor based on the clinical value (such as the prognosis) for the individual. For example, based on the tumor being classified as a low-risk class by the tumor analysis model, an apparatus may recommend chemotherapy with a lower frequency, at a later date, and/or with a lower dosage. Based on the tumor being classified as a high-risk class by the tumor analysis model, an apparatus may recommend more aggressive treatment of the tumor, such chemotherapy with a higher frequency, at an earlier date, and/or with a higher dosage. Some example embodiments may also display, for the user, an explanation of the basis of the determination; a set of options for further testing; and/or a recommendation of one or more options to be considered by the individual and/or a healthcare provider. Many such types of classification and output of clinical values for the individual and information about the tumor may be provided in some example embodiments.

H. Technical Effects

Some example embodiments that feature analysis using distribution-based machine learning classifiers may exhibit a variety of technical effects.

A first example of a technical effect that may be exhibited by some example embodiments is a new type of input classification based upon distribution, which may be difficult to achieve through other machine learning models. For example, as shown in FIG. 9, an image-based tumor classification model as disclosed herein may be capable of classifying tumors with reasonable accuracy. As further shown in FIGS. 11 and 12, a combined model that includes both image-based analysis (for example, based on a convolutional neural network and classification by a Gaussian mixture model) and regression-based analysis of clinical features (for example, based on a Cox proportional hazards model) may be capable of greater classification accuracy than either model used alone. In some scenarios, the use of machine learning models, including a visualization and/or explanation of the basis for such determinations of the clinical value for the individual (such as an indication of the image features and clinical features that contribute to the determination of the prognosis), may provide an automated process for providing clinical values that provide diagnostic, prognostic, and/or therapeutic information, and that a caregiver may utilize to choose a healthcare regimen of an individual.

A second example of a technical effect that may be exhibited by some example embodiments is a more efficient allocation of resources based upon such analyses. For example, classification of tumors based on automated techniques may reduce the volume and/or dependency of clinical and pathology resources applied to diagnose and classify tumors and to determine clinical values (such as prognoses) of individuals. Such economy of resources may also involve a faster classification process than may be systematically achievable by classification processes performed by individuals.

I. EXAMPLE EMBODIMENTS

Figure 13:
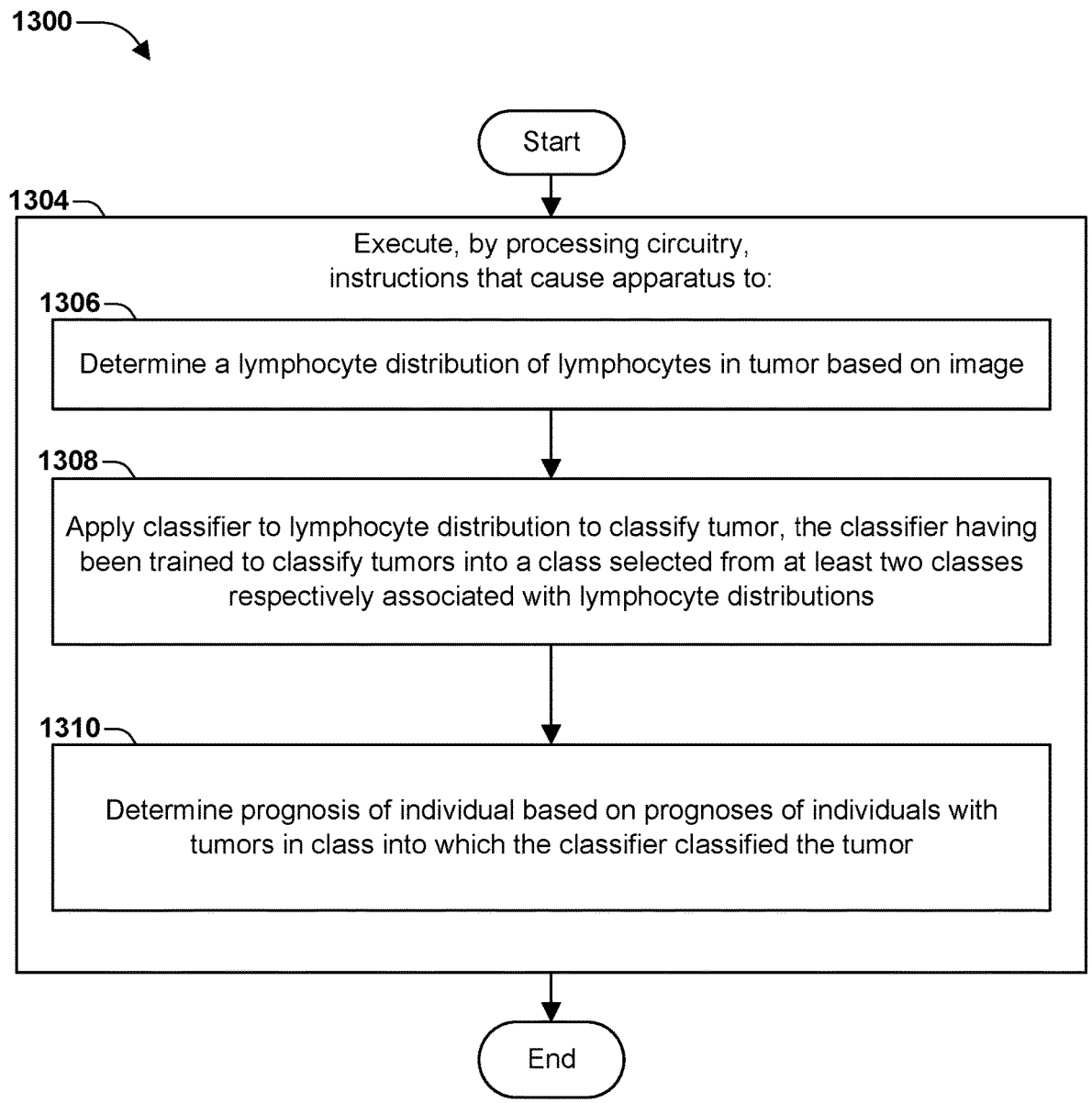
FIG. 13 is a flow diagram of a first example method, in accordance with some example embodiments.

FIG. 13 is a flow diagram of a first example method 1300, in accordance with some example embodiments.

The first example method 1300 may be implemented, for example, as a set of instructions that, when executed by processing circuitry of an apparatus, cause the apparatus to perform each of the elements of the first example method 1300. The first example method 1300 may also be implemented, for example, as a set of instructions that, when executed by processing circuitry of an apparatus, cause the apparatus to provide a system for components, including an image evaluator, a classifier, and a tumor evaluator, that interoperate to provide a system for classifying tumors.

The first example method 1300 includes executing 1304, by processing circuitry of an apparatus, instructions that cause the apparatus to perform a set of elements.

For example, the execution of the instructions may cause the apparatus to determine 1306 a lymphocyte distribution of lymphocytes in the tumor based on the image.

For example, the execution of the instructions may cause the apparatus to apply 1308 a classifier to the lymphocyte distribution to classify the tumor, the classifier having been trained to classify tumors into a class selected from at least two classes respectively associated with lymphocyte distributions.

For example, the execution of the instructions may cause the apparatus to determine 1310 the clinical value (such as the prognosis) for the individual based on prognoses of individuals with tumors in the class into which the classifier classified the tumor.

In this manner, the execution of the instructions by the processing circuitry may cause the apparatus to perform the elements of the first example method 1300, and so the first example method 1300 ends.

Figure 14:
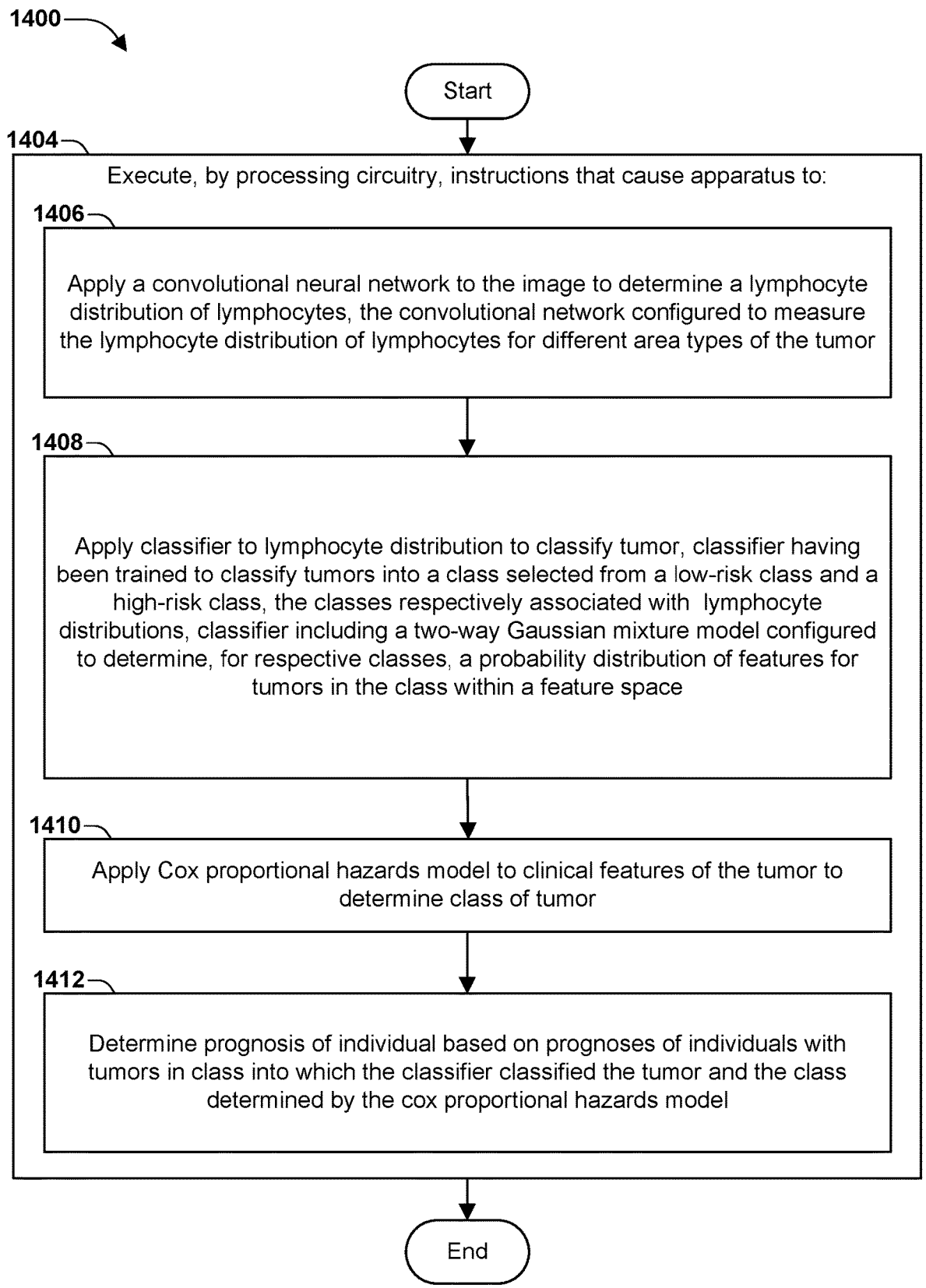
FIG. 14 is a flow diagram of a second example method, in accordance with some example embodiments.

FIG. 14 is a flow diagram of a second example method, in accordance with some example embodiments.

The second example method 1400 may be implemented, for example, as a set of instructions that, when executed by processing circuitry of an apparatus, cause the apparatus to perform each of the elements of the second example method 1400. The second example method 1400 may also be implemented, for example, as a set of instructions that, when executed by processing circuitry of an apparatus, cause the apparatus to provide a system for components, including an image evaluator, a classifier, and a tumor evaluator, that interoperate to provide a system for classifying tumors.

The second example method 1400 includes executing 1404, by processing circuitry of an apparatus, instructions that cause the apparatus to perform a set of elements.

For example, the execution of the instructions may cause the apparatus to apply 1406 a convolutional neural network to the image to determine a lymphocyte distribution of lymphocytes in the tumor, wherein the convolutional neural network is configured to measure the lymphocyte distribution of lymphocytes for different area types of the image.

For example, the execution of the instructions may cause the apparatus to apply 1408 a classifier to the lymphocyte distribution to classify the tumor, wherein the classifier has been trained to classify tumors into a class selected from a low-risk class and a high-risk class, the classes respectively being associated with lymphocyte distributions, and the classifier including a two-way Gaussian mixture model configured to determine, for respective classes, a probability distribution of features for tumors in the class within a feature space.

For example, the execution of the instructions may cause the apparatus to apply 1410 a Cox proportional hazards model to clinical features of the tumor to determine a class of the tumor.

For example, the execution of the instructions may cause the apparatus to determine 1412 the clinical value (such as the prognosis) for the individual based on the prognoses of individuals with tumors in the class into which the classifier classified the tumor and the class determined by the Cox proportional hazards model.

In this manner, the execution of the instructions by the processing circuitry may cause the apparatus to perform the elements of the second example method 1400, and so the second example method 1400 ends.

Figure 15:
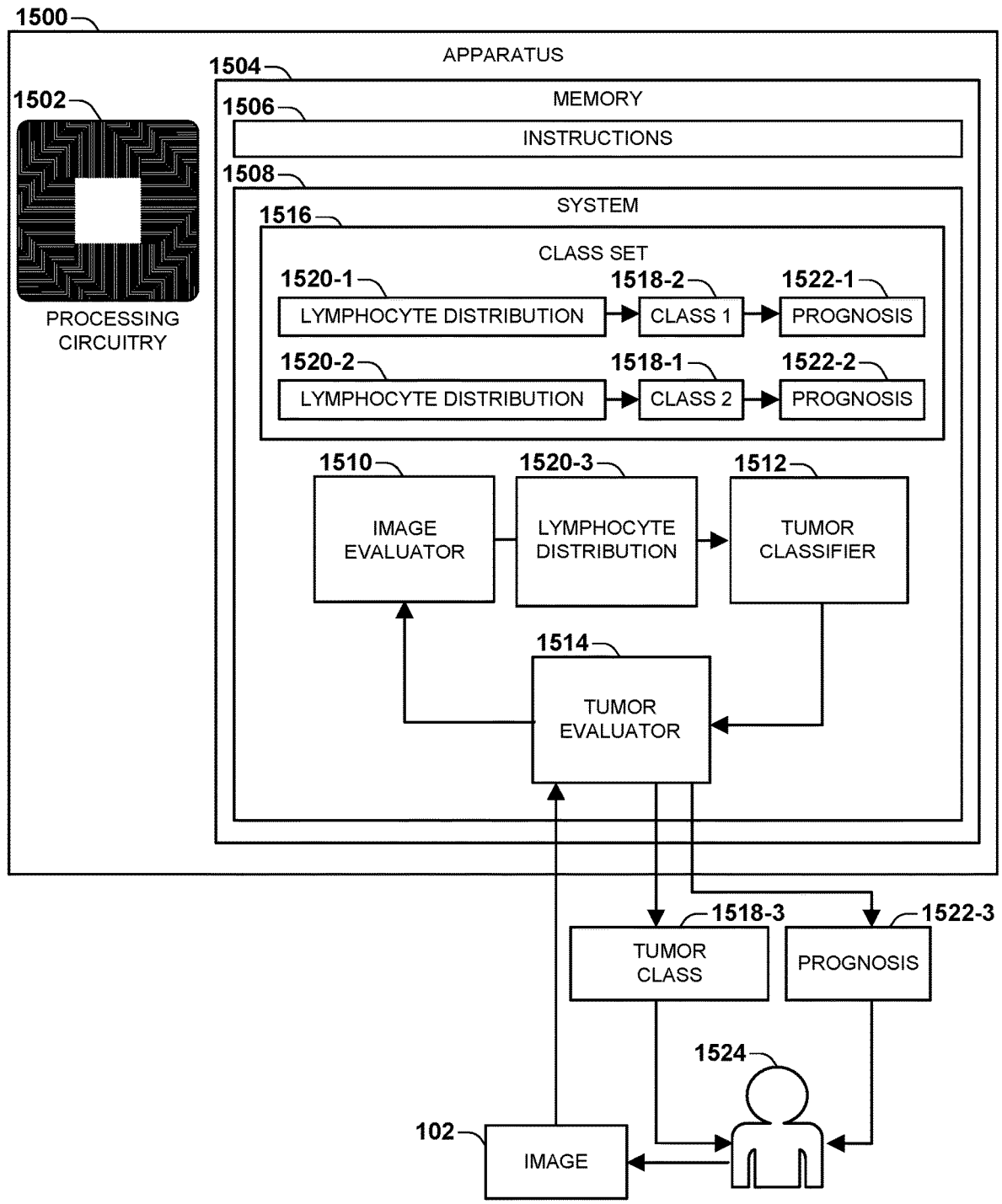
FIG. 15 is a component block diagram of an example apparatus, in accordance with some example embodiments.

FIG. 15 is a component block diagram of an example apparatus, in accordance with some example embodiments.

As shown in FIG. 15, an example apparatus 1500 may include processing circuitry 1502 and a memory 1504. The memory 1504 may store instructions 1506 that, when executed by the processing circuitry 1502, cause the example apparatus 1500 to determine a clinical value (such as a prognosis) for an individual based on a tumor shown in an image 102 in accordance with some example embodiments. In some example embodiments, execution of the instructions 1506 may cause the example apparatus 1500 to instantiate and/or use a set of components of a system 1508. While FIG. 15 illustrates one such system 1508, some example embodiments may system 1508 may embody any of the methods disclosed herein.

The example system 1508 of FIG. 15 includes an image evaluator 1510 that is configured to determine a lymphocyte distribution of lymphocytes in the image 102. For example, a class set 1516 may associate respective lymphocyte distributions 1520-1, 1520-2 with different classes 1518-1, 1518-2 of tumors, each class 1518 being associated with a prognosis 1522-1, 1522-2.

The example system 1508 of FIG. 15 includes a tumor classifier 1512 configured to classify tumors into a class selected from the at least two classes 1518 respectively associated with the lymphocyte distributions 1520.

The example system 1508 of FIG. 15 includes a tumor evaluator 1514 that is configured to determine a clinical value (such as a prognosis) for an individual based on a tumor in the image 102 by invoking the image evaluator 1510 with the image 102 to determine the lymphocyte distribution 1520-3 of lymphocytes in the tumor, invoke the tumor classifier 1512 to classify the tumor into a class 1518 based on the lymphocyte distribution 1520-3, and output, for a user 1524, a clinical value (such as a prognosis) for the individual based on the prognoses 1522 of tumors in the class 1518-3 into which the tumor classifier 1512 classified the tumor.

In this manner, the example apparatus 1500 and example system 1508 provided thereon may classify the tumor in accordance with some example embodiments.

Figure 16:
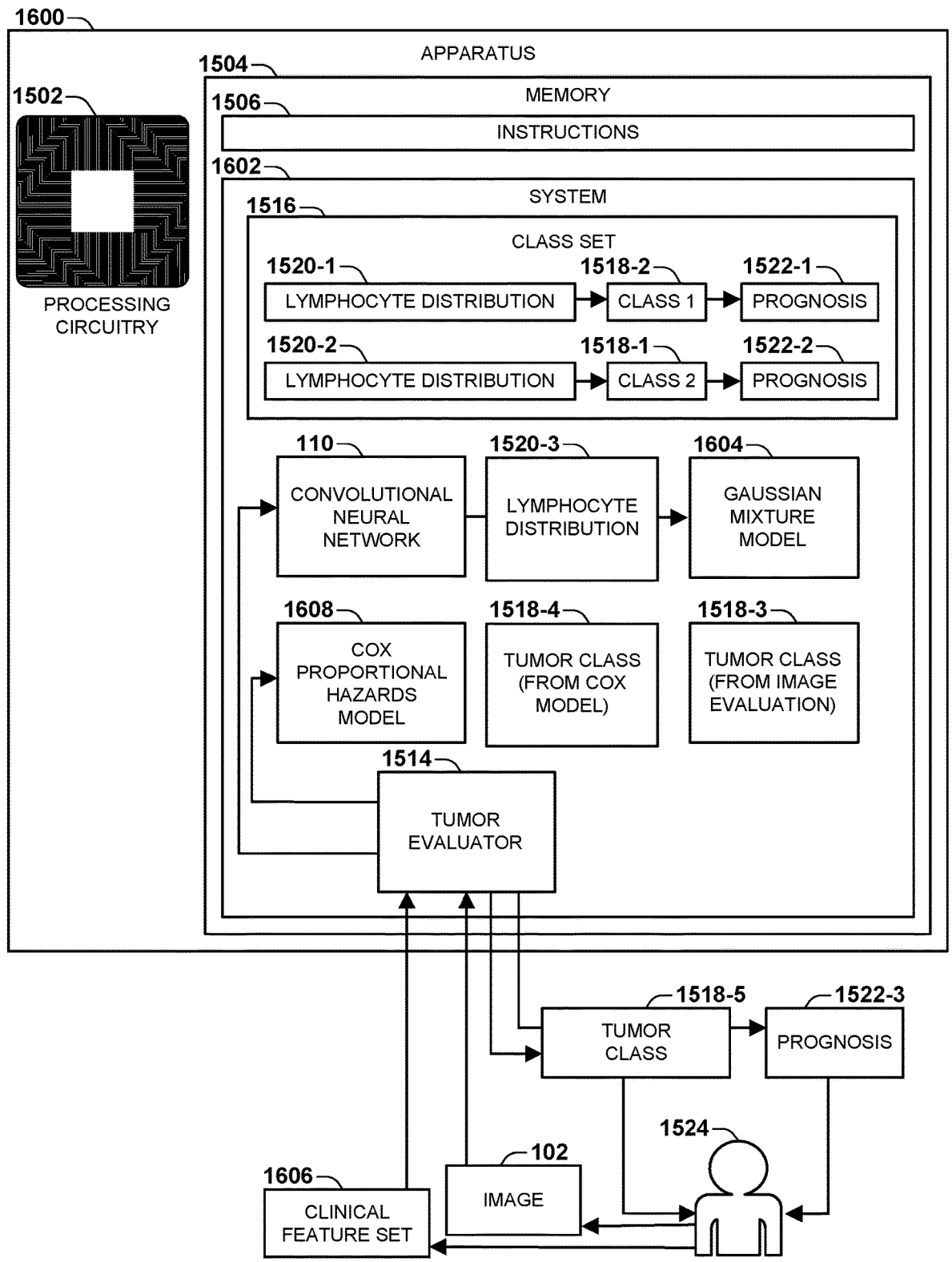
FIG. 16 is a component block diagram of another example apparatus, in accordance with some example embodiments.

FIG. 16 is a component block diagram of another example apparatus, in accordance with some example embodiments.

As shown in FIG. 16, an example apparatus 1600 may include processing circuitry 1502 and a memory 1504. The memory 1504 may store instructions 1506 that, when executed by the processing circuitry 1502, cause the example apparatus 1600 to determine a clinical value (such as a prognosis) for an individual based on a tumor shown in an image 102 in accordance with some example embodiments. In some example embodiments, execution of the instructions 1506 may cause the example apparatus 1600 to instantiate and/or use a set of components of a system 1602.

The example system 1602 of FIG. 16 includes a convolutional neural network 110, as an image evaluator, that is configured to determine a lymphocyte distribution of lymphocytes in the image 102 by measuring the lymphocyte distribution of lymphocytes for different area types of the image 102. For example, a class set 1516 may associate respective lymphocyte distributions 1520-1, 1520-2 with different classes 1518-1, 1518-2 of tumors, including a low-risk tumor class and a high-risk tumor class, each class 1518 being associated with a prognosis 1522-1, 1522-2.

The example system 1602 of FIG. 16 includes a two-way Gaussian mixture model 1604, as a tumor classifier, that is configured to determine, for respective classes 1518, a probability distribution of features for tumors in the class 1518 within a feature space 606.

The example system 1602 of FIG. 16 includes a Cox proportional hazards model 1608 configured to a clinical features set 1606 of clinical features to determine a class of the tumor.

The example system 1602 of FIG. 16 includes a tumor evaluator 1514 that is configured to determine a clinical value (such as a prognosis) for an individual based on a tumor in the image 102 of the tumor by invoking the convolutional neural network 110 with the image 102 to determine the lymphocyte distribution 1520-3 of lymphocytes in the tumor, invoke the Gaussian mixture model 1604 to classify the tumor into a class 1518-3 based on the lymphocyte distribution 1520-3, invoke the Cox proportional hazards model 1608 with the clinical feature set 1606 for the tumor to determine a tumor class 1518-4, and output, for a user 1524, a clinical value (such as a prognosis) for the individual based on the prognoses 1522 of tumors in the class 1518-5 into which the tumor classifier 1512 classified the tumor based on the prognoses for the individuals with tumors in the class 1518-3 into which the Gaussian mixture model 1604 classified the tumor and the tumor class 1518-4 determined by the Cox proportional hazards model 1608.

In this manner, the example apparatus 1600 and example system 1602 provided thereon may classify the tumor in accordance with some example embodiments.

As shown in FIGS. 15 and 16, example apparatuses 1500, 1600 may include processing circuitry 1502 that is capable of executing instructions. The processing circuitry 1502 may include, such as hardware including logic circuits; a hardware/software combination, such as a processor executing software; or a combination thereof. For example, a processor may include, but is not limited to, a central processing unit (CPU), a graphics processing unit (GPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

As further shown in FIGS. 15 and 16, example apparatuses 1500, 1600 may include a memory 1504 storing instructions 1506. The memory 1504 may include, for example, random-access memory (RAM), read-only memory (ROM), an erasable programmable read-only memory (EPROM), an electrically erasable programmable read-only memory (EEPROM), etc. The memory 1504 may be volatile, such as system memory, and/or nonvolatile, such as a hard disk drive, a solid-state storage device, flash memory, or magnetic tape. The instructions 1506 stored in the memory 1504 may be specified according to a native instruction set architecture of a processor, such as a variant of the IA-32 instruction set architecture or a variant of the ARM instruction set architecture, as assembly and/or machine-language (e.g., binary) instructions; instructions of a high-level imperative and/or declarative language that is compilable and/or interpretable to be executed on a processor; and/or instructions that are compilable and/or interpretable to be executed by a virtual processor of a virtual machine, such as a web browser. A set of non-limiting examples of such high-level languages may include, for example: C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Swift, Eiffel, Smalltalk, Erlang, Ruby, Flash®, Visual Basic®, Lua, MATLAB, SIMULINK, and Python®. Such instructions 1506 may also include instructions for a library, resource, platform, application programming interface (API), or the like that is utilized in determining a clinical value (such as a prognosis) for an individual based on a tumor shown in an image.

As shown in FIGS. 15 and 16, example systems 1508, 1602 may be organized in a particular manner, for example, to allocate some functionality to each component of a system. Some example embodiments may implement each such component in various ways, such as software, hardware (e.g., processing circuitry), or a combination thereof. In some example embodiments, the organization of the system may vary as compared with some other example embodiments, including the example systems 1508, 1602 shown in FIGS. 15 and 16. For example, some example embodiments may include a system featuring a different organization of components, such as renaming, rearranging, adding, partitioning, duplicating, merging, and/or removing components, sets of components, and relationships thereamong, without departing from the scope of the present disclosure. All such variations that are reasonably technically and logically possible, and that are not contradictory with other statements, are intended to be included in this disclosure, the scope of which is to be understood as being limited only by the claims.

Figure 17:
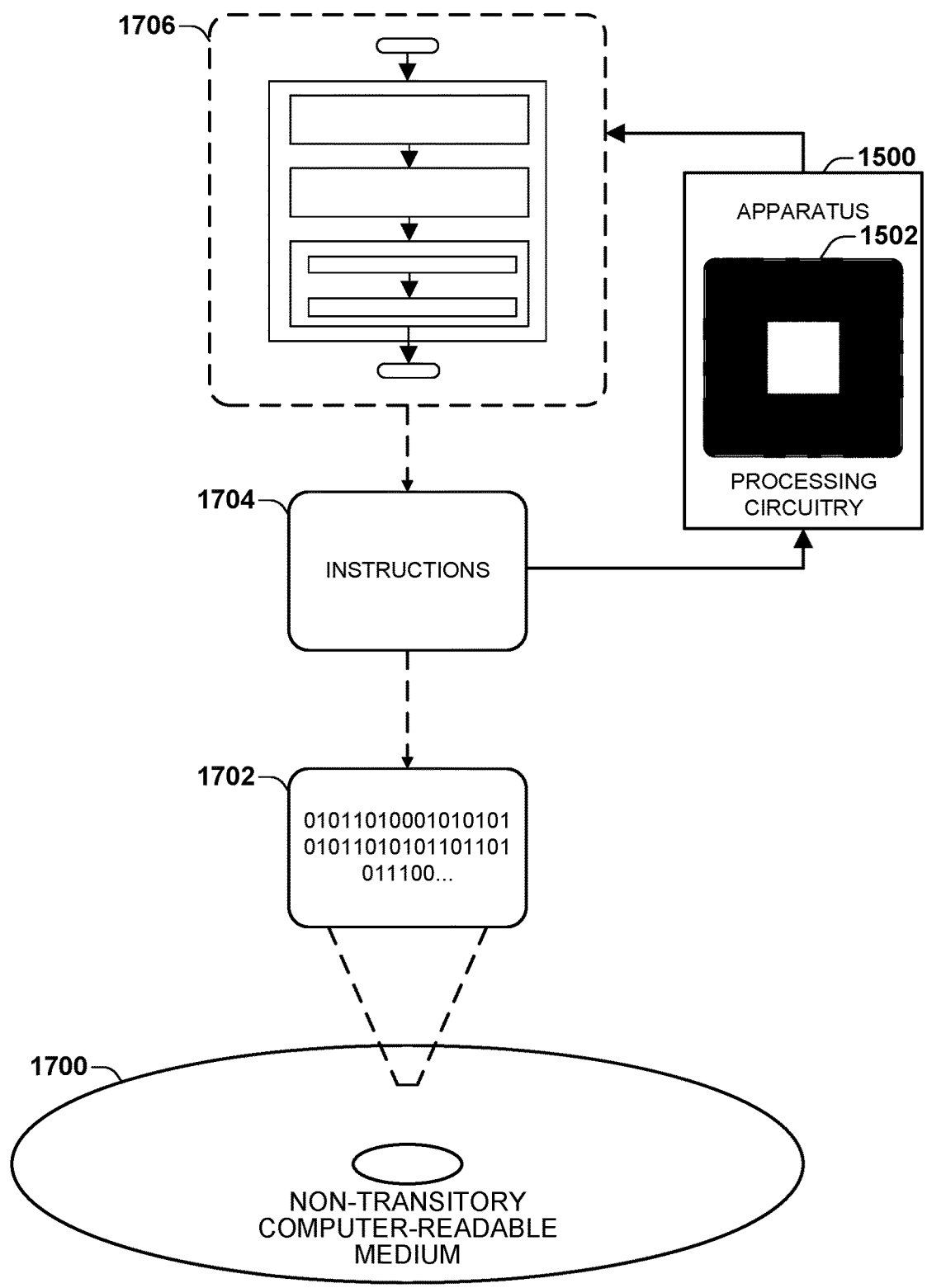
FIG. 17 is an illustration of an example computer-readable medium, in accordance with some example embodiments.

FIG. 17 is an illustration of an example computer-readable medium 1700, in accordance with some example embodiments.

As shown in FIG. 17, the non-transitory computer-readable medium 1700 may store binary data 1702 encoding a set of instructions 1704 that, when executed by processing circuitry 1502 of an example apparatus 1500, 1600, cause the example apparatus 1500, 1600 to determine a clinical value (such as a prognosis) for an individual based on a tumor shown in an image in accordance with some example embodiments. As a first such example, the instructions 1704 may encode the elements of an example method 1706, such as the first example method 1300 of FIG. 13. As a second such example, the instructions 1704 may encode the elements of the second example method 1400 of FIG. 14. As a third such example, the instructions 1704 may encode the components of the first example system 1508 of FIG. 15. As a fourth such example, the instructions 1704 may encode the components of the second example system 1602 of FIG. 16.

In some example embodiments, a system may include image evaluating means for determining a lymphocyte distribution of lymphocytes in an image. For example, the image evaluating means may be or may include one or more convolutional neural networks and/or any of the other image evaluation models discussed herein. The system may include classifying means for classifying tumors into a class selected from at least two classes respectively associated with lymphocyte distributions. For example, the classifying means may be or may include one or more Gaussian mixture models and/or any of the other classifiers discussed herein.

The system may include a tumor evaluator means for determining a clinical value (such as a prognosis) for an individual based on a tumor in an image by invoking the image evaluating means with the image to determine the lymphocyte distribution of lymphocytes in the tumor, invoking the classifier to classify the tumor into a class based on the lymphocyte distribution, and outputting a clinical value (such as a prognosis) for the individual based on prognoses of individuals with tumors in the class into which the classifier classified the tumor. For example, the tumor evaluator means may be or may include a classifier, such as a neural network, a soft- or hard-margin support vector machine, and/or any of the other classifiers discussed herein. For example, the tumor evaluator means may be or may include a display device such as a liquid crystal display (LCD), light-emitting diode (LED), or organic light-emitting diode (OLED) display; a communication interface such as a webserver, an email server, or a text messaging server; and/or any other output device disclosed herein.

J. Variations

Some example embodiments of the present disclosure may include variations in many aspects, and some variations may present additional advantages and/or reduce disadvantages with respect to other variations of these sand other techniques. Moreover, some variations may be implemented in combination, and some combinations may feature additional advantages and/or reduced disadvantages through synergistic cooperation. The variations may be incorporated in some example embodiments (e.g., the first example method of FIG. 13, the second example method of FIG. 14, the example apparatuses 1500, 1600 and example systems 1508, 1602 of FIGS. 15 and 16, and/or the example non-transitory computer-readable medium 1700 of FIG. 17) to confer individual and/or synergistic advantages upon such example embodiments.

F1. Scenarios

Some example embodiments may be utilized in a variety of scenarios that involve an analysis of input using distribution-based machine learning models. For example, some example embodiments may use the disclosed techniques to classify tumors for endeavors in various fields of life sciences, including healthcare and biomedical research. The tumor classification techniques disclosed herein may be applicable to a wide variety of cancer types, including (without limitation) lung cancer tumors, pancreatic adenocarcinoma tumors, and/or breast cancer tumors. A clinical pathology laboratory may use such techniques to determine tumor classes of tumor samples, and/or to compare or validate determinations of tumor classes by individuals and/or other automated processes. A researcher may use such techniques to determine tumor classes of tumors in images of a research data set, which may be from human patients or from human or non-human experimental subjects, where such research may involve further techniques for classifying tumors, identifying the prevalence and classes of tumors in different demographics, identifying risk factors that are correlated with tumors of different tumor classes, projecting survivability, for determining or comparing the effectiveness of treatment options. A clinician may use the results of the classification to evaluate the diagnostic, prognostic, and/or treatment options for an individual with a tumor, and/or to explore and understand the correlation of various risk factors with different tumor classes and the prognoses of individuals with such tumors. Many such scenarios may be devised in which the disclosed techniques may be utilized.

F2. Determining Feature Presence and Distribution

In some example embodiments, machine learning models, including deep learning models, may be used for the detection of various features of various inputs. In various example embodiments, such machine learning models may be used to determine the feature map 118 of an image 102, for example, by generating and applying a mask set 300 of masks 302; to determine a distribution of the features, such as clusters 204; to perform a classification 402 of areas of an image, such as area types based on anatomic features and/or tissue types; to perform a measurement 304 of a feature, such as a concentration (e.g., percentage area of an entire image) of a feature or an area type, for example, a lymphocyte density range estimation 404, using techniques such as binning; to generate a density map, such as a lymphocyte density map 406; to choose a set of features to be used to classify images 102 or a particular image 102, such as performing the selection process 700 of FIG. 7 to select a feature subset; to classify an image 102 of a tumor based on an image feature set or image feature subset; to select a clinical feature subset from a the values of clinical features 706 of a clinical feature set for an individual or a tumor; to determine the values of clinical features 706 of a clinical feature set for an individual and/or a tumor; to determine a class of a tumor, such as by preparing and applying a Cox proportional hazards model to clinical features of the tumor; to determine a class of a tumor based on image features of the tumor (such as the output of a Gaussian mixture model) and/or clinical features of the tumor or the individual (such as the output of a Cox proportional hazards model); to project a survivability for an individual based on a classification of a tumor of the individual; and/or to generate one or more outputs, including visualizations, of such determinations. Each of these features and other features of some example embodiments may be performed, for example, by a machine learning model; by a plurality of machine learning models of a same or similar type, such as random forests, or convolutional neural networks that evaluate different parts of an image or that perform different tasks on an image; and/or by a combination of machine learning models of different types. As one such example, in a boosting ensemble, a first machine learning model performs classification based on the output of other machine learning models.

As a first such example, the presence of the feature (e.g., an activation within a feature map, and/or a biological activation of lymphocytes) may be determined in various ways. For example, where an input further includes an image 102, the determining of the presence of the feature may be performed by applying at least one convolutional neural network 110 to the image 102 and receiving, from the at least one convolution neural network 110, a feature map 118 indicating the presence of the feature of the input. That is, a convolutional neural network 110 may be applied to an image 102 to identify clusters of pixels 108 in which a feature is apparent. For example, cell-counting convolutional neural networks 110 may be applied to count cells in a tissue sample, where such cells may be lymphocytes. In such scenarios, the tissue sample may be subjected to an assay, such as a dye or a luminescent (such as fluorescent) agent, and a collection of images 102 of the tissue sample may be selective for the cells and may therefore not include other visible components of the tissue sample. The image 102 of the tissue sample may then be subjected to a machine learning model (such as a convolutional neural network 110) that may be configured (e.g., trained) to detect shapes such as circles that are indicative of the selected cells, and may output a count in the image 102 and/or for different areas of the image 102. Notably, the convolutional neural network 110 in this case may not be configured and/or used to further detect an arrangement of such features, for example, a number, orientation, and/or positioning of lymphocytes with respect to other lymphocytes; rather, the counts of respective portions of the image 102 may be compiled into a distribution map that may be processed together with a tumor mask to determine the distribution of lymphocytes as being tumor-invasive, tumor-adjacent, or elsewhere in the tissue sample. Some example embodiments may use a machine learning model other than a convolutional neural network to detect the presence of a feature, such as (e.g.) a non-convolutional neural network such as a fully-connected network or a perceptron network or a Bayesian classifier.

As a second such example, the distribution of the feature may be determined in a variety of ways. As a first example, where the input further includes an image 102 illustrating a tissue region of an individual, determining the distribution of the feature further may include determining an area type (e.g., tumor or non-tumor) for each area of the image, and determining the distribution based on the area type of each area of the image. The distribution of detected lymphocytes, including lymphocyte counts, may then be determined based upon the types of tissue in which such counts occur. That is, the distribution may be determined by tabulating counts of lymphocytes for tumor areas, tumor-adjacent areas (such as stroma), and non-tumor areas of the image 102. As another such example, the determining may include determining a boundary of the tissue region within the image 102, and determining the distribution based on the boundary of the tissue region within the image 102. That is, the boundaries of the areas of the image 102 that are classified as tumor may be determined (e.g., by a convolutional neural network 110 and/or a human), and an example embodiment may tabulate the counts of lymphocytes for all of the areas of the image that are within the determined boundaries of the tumor. As yet another example, the tissue region of the image including at least two areas, and determining the distribution may include determining a count of lymphocytes within each area of the tissue region and determining the distribution based on the count within each area of the tissue region. For example, determining the count within each tissue region may include determining a density of the count of lymphocytes within each area, and then determining the distribution based on the count within each area. An example is shown in FIG. 3, in which a first convolutional neural network 110-1 is provided to classify areas as tumor vs. non-tumor areas and a second convolutional neural network 110-2 is provided to estimate a density range of lymphocytes.

As a third such example, the processing of an image 102 to determine the presence of a feature and/or the distribution of a feature may occur in several ways. For example, some example embodiments may be configured to partition an image 102 into a set of areas of the same or varying sizes and/or shapes, such as based on a number of pixels or a corresponding physical size (e.g., 100-micrometer square areas), and/or based on similarity grouping (e.g., identifying areas of similar appearance within the image 102). Some example embodiments may be configured to classify each area (for example, as tumor, tumor-adjacent, or non-tumor), and/or to determine the distribution by tabulating the presence of the feature (e.g., a count) within each area of a certain area type to determine the distribution of lymphocytes. Alternatively, a counting process may be applied to each area, and each area may be classified based on a count (e.g., high-lymphocyte vs. low-lymphocyte areas). As yet another example, the distributions may be determined in a parametric manner, such as according to a selected distribution type or kernel that a machine learning model may fit to the distribution of the feature in the input (e.g., a Gaussian mixture model may be applied to determine Gaussian distributions of subsets of the feature). Other distribution models may be applied, including parametric distribution models such as chi-square fit, a Poisson distribution, and a beta distribution and non-parametric distribution models such as histograms, binning, and kernel methods.

As a fourth such example, many forms of classifiers may be used, such as Bayesian (including naïve Bayesian) classifiers; Gaussian classifiers; probabilistic classifiers; principal component analysis (PCA) classifiers; linear discriminant analysis (LDA) classifiers; quadratic discriminant analysis (QDA) classifiers; single-layer or multiplayer perceptron networks; convolutional neural networks; recurrent neural networks; nearest-neighbor classifiers; linear SVM classifiers; radial-basis-function kernel (RBF) SVM classifiers; Gaussian process classifiers; decision tree classifiers, including random forest classifiers; and/or restricted or unrestricted Boltzmann machines, among others. Examples of convolutional neural network classifiers include, without limitation, LeNet, ZfNet, AlexNet, BN-Inception, CaffeResNet-101, DenseNet-121, DenseNet-169, DenseNet-201, DenseNet-161, DPN-68, DPN-98, DPN-131, FBResNet-152, GoogLeNet, Inception-ResNet-v2, Inception-v3, Inception-v4, MobileNet-v1, MobileNet-v2, NASNet-A-Large, NASNet-A-Mobile, ResNet-101, ResNet-152, ResNet-18, ResNet-34, ResNet-50, ResNext-101, SE-ResNet-101, SE-ResNet-152, SE-ResNet-50, SE-ResNeXt-101, SE-ResNeXt-50, SENet-154, ShuffleNet, SqueezeNet-v1.0, SqueezeNet-v1.1, VGG-11, VGG-11_BN, VGG-13, VGG-13_BN, VGG-16, VGG-16_BN, VGG-19, VGG-19 BN, Xception, DelugeNet, FractalNet, WideResNet, PolyNet, PyramidalNet, and U-net.

In some example embodiments, classification may include regression, and the term "classification" as used herein is intended to include some example embodiments that perform regression as an alternative to, or in addition to, a selection of a class. For example, some example embodiments may feature regression as an alternative to or additional to classification. As a first such example, a determination of a presence of a feature may include a regression of the presence of the feature, for example, a numerical value indicating a density of the feature in an input. As a second such example, a determination of a distribution of a feature may include a regression of the distribution of the feature, such as a variance of the regression-based density determined for the input. As a third such example, the choosing may include performing a regression of the distribution of the feature and choosing a regression value for the distribution of the feature. Such regression aspects may be performed instead of classification or in addition to a classification (for example, determining both a presence of the feature and a density of the feature in an area of an image). Some example embodiments may involve regression-based machine learning models, such as Bayesian linear or nonlinear regression, regression-based artificial neural networks such as convolutional neural network regression, support vector regression, and/or decision tree regression.

Each classifier may be linear or nonlinear; for example, a nonlinear classifier may be provided (e.g., trained) to perform a linear classification based upon a kernel transform in a nonlinear space, that is, a transformation of linear values of a feature vector into nonlinear features. The classifiers may include a variety of techniques to promote accurate generalization and classification, such as input normalization, weight regularization, and/or output processing, such as a softmax activation output. The classifiers may use a variety of techniques to promote efficient training and/or classification. For example, a two-way Gaussian mixture model may be used in which a same size of the Gaussian distributions is selected for each dimension of the feature space, which may reduce the search space as compared with other Gaussian mixture models in which the sizes of the distribution for different dimensions of the feature space may vary.

Each classifier may be trained to perform classification in a particular manner, such as supervised learning, unsupervised learning, and/or reinforcement learning. Some example embodiments may include additional training techniques to promote generalization, accuracy, and/or convergence, such as validation, training data augmentation, and/or dropout regularization. Ensembles of such classifiers may also be utilized, where such ensembles may be homogeneous or heterogeneous, and wherein the classification 122 based on the outputs of the classifiers may be produced in various ways, such as by consensus, based on the confidence of each output (e.g., as a weighted combination), and/or via a stacking architecture such as based on one or more blenders. The ensembles may be trained independently (e.g., a bootstrap aggregation training model, or a random forest training model) and/or in sequence (e.g., a boosting training model, such as Adaboost). As an example of a boosting training model, in some support vector machine ensembles, at least some of the support vector machines may be trained based on an error of a previously trained support vector machine; e.g., each successive support vector machine may be trained particularly upon the inputs of the training data set 100 that were incorrectly classified by previously trained support vector machines.

As a fifth such example, various forms of classification 122 may be produced by the one or more classifiers. For example, a perceptron or binary classifier may output a value indicating whether an input is classified as a first class 106 or a second class 106, such as whether an area of an image 102 is a tumor area or a non-tumor area. As another example, a probabilistic classifier may be configured to output a probability that the input is classified into each class 106 of the class set 104. Alternatively or additionally, some example embodiments may be configured to determine a probability of classifying the input into each class 106 of the class set 104, and to choose, from a class set 104 including at least two classes 106, a class 106 of the input, the choosing being based on probabilities of classifying the input into each class 106 of the class set 104. For example, a classifier may output a confidence of the classification 122, e.g., a probability of classification error, and/or may refrain from outputting a classification 122 based upon poor confidence, e.g., a minimum-risk classifier. For example, in areas of an image 102 that are not clearly identifiable as tumor or non-tumor, a classifier may be configured to refrain from classifying the area in order to promote accuracy in the calculated distribution of lymphocytes in areas that may be identified as tumor and non-tumor with acceptable confidence.

As a sixth such example, some example embodiments may be configured to process the distribution of a feature with a linear or nonlinear classifier, and may receive, from the linear or nonlinear classifier, a classification 122 of the class 106 of the input. For example, a linear or nonlinear classifier may include a support vector machine ensemble of at least two support vector machines, and some example embodiments may be configured to receive the classification 122 by receiving, from each of the at least two support vector machines, a candidate classification 122, and to determine the classification 122 based on a consensus of the candidate classifications 122 among the at least two support vector machines.

As a seventh such example, some example embodiments may be configured to use a linear or nonlinear classifier (including a set or ensemble of classifiers) to perform a classification 122 of an input in a variety of ways. For example, an input may be partitioned into areas, and for each input portion, an example embodiment may use a classifier to classify the input portion according to an input portion type selected from a set of input portion types (e.g., performing a classification 122 of portions of an image 102 of a tumor as tumor areas vs. non-tumor areas, such as shown in the example of FIG. 3). The example embodiment may then be configured to choose, from a class set including at least two classes, a class of the input, the choosing based on the distribution of the feature for each input portion of an input portion type and the distribution of the feature for each input portion type of the set of input portion types (e.g., classifying areas of tumor-invasive lymphocytes (TIL), tumor-adjacent lymphocytes such as in stroma, high-activation lymphocyte areas, and/or low-activation lymphocyte areas).

As an eighth such example, some example embodiments may be configured to perform a distribution classification by determining a variance of the distribution of the feature of the input, e.g., the variance of the distribution over the areas of an input such as an image 102. Some example embodiments may then be configured to perform classification 122 by choosing, from a class set 104 including at least two classes 106, a class 106 of the input, the choosing being based on the variance of the distribution of the feature of the input and the variance of distribution of the feature for each class 106 of the class set 104. For example, some example embodiments may be configured to determine a class of a tumor based, at least in part, upon the variance of the distribution of lymphocytes over the different areas of the image.

As a ninth such example, some example embodiments may use different training and/or testing to generate and validate the machine learning models. For example, training may be performed using heuristics such as stochastic gradient descent, nonlinear conjugate gradient, or simulated annealing. Training may be performed offline (e.g., based on a fixed training data set 100) or online (e.g., continuous training with new training data). Training may be evaluated based on various metrics, such as perceptron error, Kullback-Leibler (KL) divergence, precision, and/or recall. Training may be performed for a fixed time (e.g., a selected number of epochs or generations), until training fails to yield additional improvement, and/or until reaching a point of convergence (for example, when classification accuracy reaches a target threshold). A machine learning model may be tested in various ways, such as k-fold cross-validation, to determine the proficiency of the machine learning model on previously unseen data. Many such forms of classification 122, classifiers, training, testing, and validation may be included and used in some example embodiments.

K. Example Computing Environment

Figure 18:
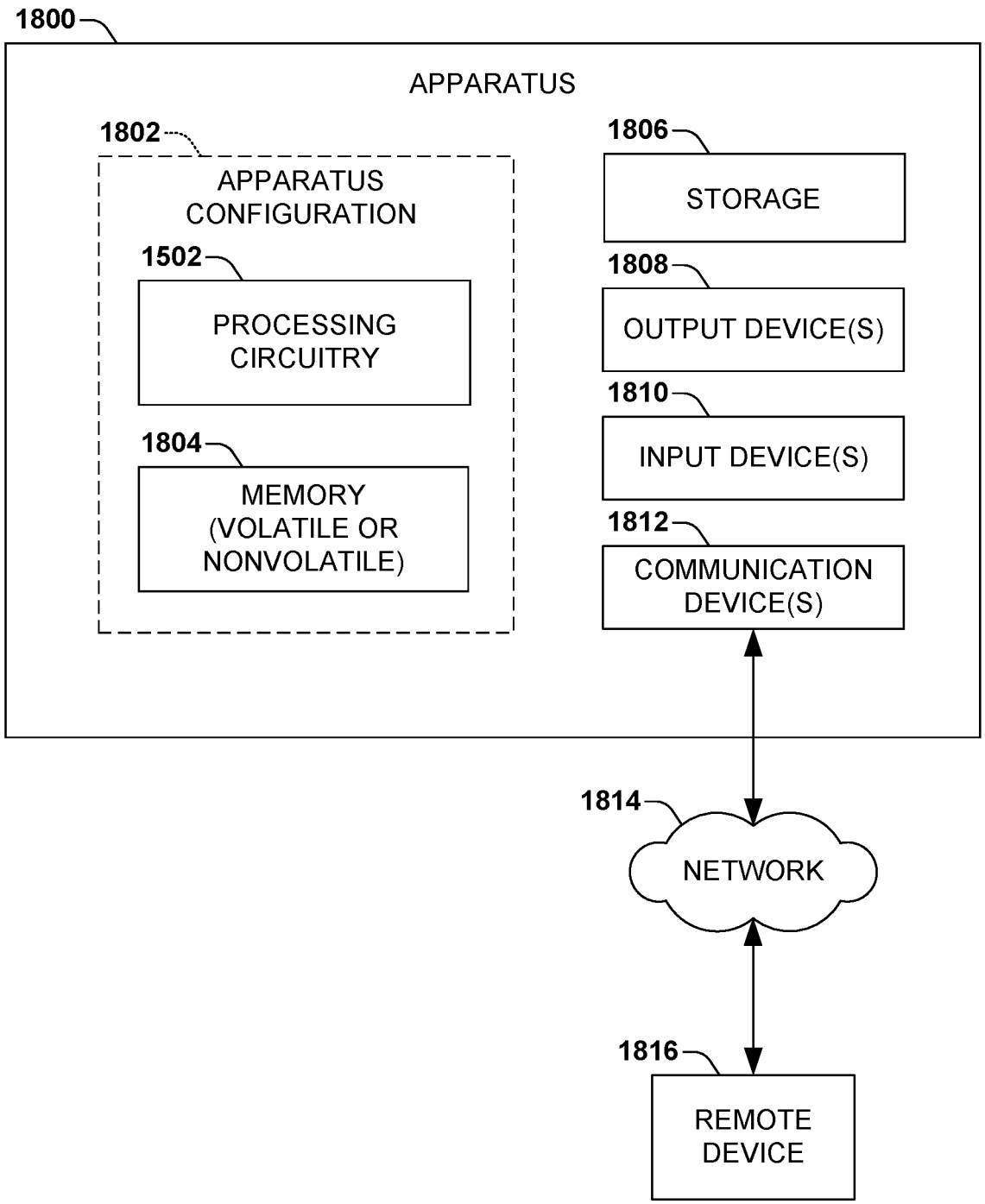
FIG. 18 is an illustration of an example apparatus in which some example embodiments may be implemented.

FIG. 18 is an illustration of an example apparatus in which some example embodiments may be implemented.

FIG. 18 and the following discussion provide a brief, general description of a suitable computing environment to implement embodiments of one or more of the provisions set forth herein. The operating environment of FIG. 18 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, media devices such as televisions, consumer electronics, embedded devices, mini computers, mainframe computers, distributed computing environments that include any of the above systems or devices, wearable computing devices (such as glasses, earpieces, wristwatches, rings, pendants, handheld and/or body-mounted cameras, clothing-integrated devices, and implantable devices), autonomous vehicles, extended reality (XR) devices such as augmented reality (AR) and/or virtual reality (VR) devices, internet-of-things (IoT) devices, and the like.

Some example embodiments may include a combination of components of the same and/or different types, such as a plurality of processors and/or processing cores in a uniprocessor or multi-processor computer; two or more processors operating in tandem, such as a CPU and a GPU; a CPU utilizing an ASIC; and/or software executed by processing circuitry.

Some example embodiments may include components of a single device, such a computer including one or more CPUs that store, access, and manage the cache. Some example embodiments may include components of multiple devices, such as two or more devices having CPUs that communicate to access and/or manage a cache. Some example embodiments may include one or more components that are included in a server computing device, a server computer, a series of server computers, server farm, a cloud computer, a content platform, a mobile computing device, a smartphone, a tablet, or a set-top box. Some example embodiments may include components that communicate directly (e.g., two or more cores of a multi-core processor) and/or indirectly (e.g., via a bus, via over a wired or wireless channel or network, and/or via an intermediate component such as a microcontroller or arbiter). Some example embodiments may include multiple instances of systems or instances that are respectively performed by a device or component, where such systems instances may execute concurrently, consecutively, and/or in an interleaved manner. Some example embodiments may feature a distribution of an instance or system over two or more devices or components.

Although not required, some example embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 18 illustrates an example of an example apparatus 1800 configured as, or to include, one or more example embodiments, such as the example embodiments provided herein. In one apparatus configuration 1802, the example apparatus 1800 may include processing circuitry 1502 and memory 1804. Depending on the exact configuration and type of computing device, memory 1804 may be volatile (such as RAM, for example), nonvolatile (such as ROM, flash memory, etc., for example) or some combination of the two.

In some example embodiments, an example apparatus 1800 may include additional features and/or functionality. For example, an example apparatus 1800 may also include additional storage (e.g., removable and/or non-removable) including, but not limited to, magnetic storage, optical storage, and the like. Such additional storage is illustrated in FIG. 18 by storage 1806. In some example embodiments, computer-readable instructions to implement one or more embodiments provided herein may be stored in the memory 1804 and/or the storage 1806.

In some example embodiments, the storage 1806 may be configured to store other computer readable instructions to implement an operating system, an application program, and the like. Computer-readable instructions may be loaded in memory 1804 for execution by processing circuitry 1502, for example. Storage may include volatile and nonvolatile, removable and non-removable media implemented in any method or technology for storage of information such as computer readable instructions or other data. Storage may include, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which may be used to store the desired information and which can be accessed by example apparatus 1800. Any such computer storage media may be part of example apparatus 1800.

In some example embodiments, an example apparatus 1800 may include input device(s) 1810 such as keyboard, mouse, pen, voice input device, touch input device, infrared cameras, video input devices, and/or any other input device. Output device(s) 1808 such as one or more displays, speakers, printers, and/or any other output device may also be included in example apparatus 1800. Input device(s) 1810 and output device(s) 1808 may be connected to example apparatus 1800 via a wired connection, wireless connection, or any combination thereof. In some example embodiments, an input device or an output device from another computing device may be used as input device(s) 1810 or output device(s) 1808 for example apparatus 1800.

In some example embodiments, an example apparatus 1800 may be connected by various interconnects, such as a bus. Such interconnects may include a Peripheral Component Interconnect (PCI), such as PCI Express, a Universal Serial Bus (USB), Firewire (IEEE 1394), an optical bus structure, and the like. In other example embodiments, components of an example apparatus 1800 may be interconnected by a network. For example, memory 1804 may include multiple physical memory units located in different physical locations interconnected by a network.

In some example embodiments, an example apparatus 1800 may include one or more communication device(s) 1812 by which the example apparatus 1800 may communicate with other devices. Communication device(s) 1812 may include, for example, a modem, a Network Interface Card (NIC), an integrated network interface, a radio frequency transmitter/receiver, an infrared port, a USB connection, or other interfaces for connecting the example apparatus 1800 to other computing devices, including remote devices 1816. Communication device(s) 1812 may include a wired connection or a wireless connection. Communication device(s) 1812 may be configured to transmit and/or receive communication media.

Those skilled in the art will realize that storage devices used to store computer readable instructions may be distributed across a network. For example, an example apparatus 1800 may communicate with a remote device 1816 via a network 1814 to store and/or retrieve computer-readable instructions to implement one or more example embodiments provided herein. For example, an example apparatus 1800 may be configured to access a remote device 1816 to download a part or all of the computer-readable instructions for execution. Alternatively, an example apparatus 1800 may be configured to download portions of the computer-readable instructions as needed, wherein some instructions may be executed at or by the example apparatus 1800 and some other instructions may be executed at or by the remote device 1816.

In this application, including the definitions below, the term "module" or the term "controller" may be replaced with the term "circuit." The term "module" may refer to, be part of, or include processing circuitry 1502 (shared, dedicated, or group) that executes code and memory hardware (shared, dedicated, or group) that stores code executed by the processing circuitry 1502.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processing circuitry 1502 may encompass a single microprocessor that executes some or all code from multiple modules. Group processing circuitry 1502 may encompass a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The example embodiments of apparatuses and methods described herein may be partially or fully implemented by a special-purpose computer created by configuring a general-purpose computer to execute one or more particular functions embodied in computer programs. The functional blocks and flowchart elements described herein may serve as software specifications, which may be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

L. Use of Terms

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any other example embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "component," "module," "system," "interface," and the like are generally intended to refer to a computer-related entity, either hardware, a combination of hardware and software, software, or software in execution. For example, a component may be, but is not limited to being, a process running on processing circuitry 1502, processing circuitry 1502, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, some example embodiments may include a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In some example embodiments, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each example embodiment provided herein.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. The articles "a" and "an" as used herein and in the appended claims may generally be construed to mean "one or more" unless specified otherwise or clear from context to be directed to a singular form.

Although the disclosure has been shown and described with respect to some example embodiments, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated some example embodiments of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A method of operating an apparatus including processing circuitry and a convolutional neural network that is trained to determine a lymphocyte distribution of lymphocytes in an area of an image, the method comprising:
    executing, by the processing circuitry, instructions that cause the apparatus to:
        receive an image depicting at least part of a tumor,
        invoke the convolutional neural network to determine a lymphocyte distribution of lymphocytes in respective areas of the tumor based on the image,
        apply a classifier to the lymphocyte distribution to classify the tumor, the classifier trained to classify tumors into a class selected from at least two classes associated with lymphocyte distributions, and
        determine a clinical value for an individual based on a set of prognosis data corresponding to individuals with tumors in the class into which the classifier classified the tumor,
        wherein the convolutional neural network is further trained to classify an area of the image as one or more area types selected from an area type set including a tumor area, a lymphocyte area, and a stroma area,
        wherein determining the lymphocyte distribution of lymphocytes in the tumor includes, for respective lymphocyte areas of the image;
            determining a distance of the lymphocyte area to one or both of a tumor area or a stroma area; and
            based on the distance, characterizing the lymphocyte area as one of tumor-infiltrating lymphocyte area, a tumor-adjacent lymphocyte area, stroma-infiltrating lymphocyte area, and stroma-adjacent lymphocyte area, and
        wherein the classifier is configured to further classify the tumor based on the characterizing of the lymphocyte area.

2. The method of claim 1, wherein the tumor is one of:
    a pancreatic adenocarcinoma tumor, and
    a breast cancer tumor.

3. The method of claim 1, wherein:
    determining the lymphocyte distribution of lymphocytes in the tumor includes, for respective stroma areas of the image,
        determining a distance of the stroma area to a tumor area, and
        based on the distance, characterizing the stroma area as one of:
            a tumor-infiltrating stroma area, and
            a tumor-adjacent stroma area; and
    the classifier further classifies the tumor based on the characterizing of the stroma area.

4. The method of claim 1, wherein the at least two classes include:
    a high-risk class of tumors that are associated with a first survival probability, and
    a low-risk class of tumors that are associated with a second survival probability that is longer than the first survival probability.

5. The method of claim 1, wherein the classifier further comprises a Gaussian mixture model configured to determine, for respective classes, a probability distribution of features for tumors in the class within a feature space, and the features of the feature space of the Gaussian mixture model are selected from a feature set including at least one of:
    a measurement of tumor areas of the image,
    a measurement of stroma areas of the image,
    a measurement of lymphocyte areas of the image,
    a measurement of tumor-infiltrating lymphocyte areas of the image,
    a measurement of tumor-adjacent lymphocyte areas of the image,
    a measurement of stroma-infiltrating lymphocyte areas of the image,
    a measurement of stroma-adjacent lymphocyte areas of the image,
    a measurement of tumor-infiltrating stroma areas of the image, and
    a measurement of tumor-adjacent stroma areas of the image.

6. The method of claim 5, wherein, from the feature set, a feature subset is selected based on a correlation of the respective classes with respective features of the subset, and the correlation of the respective classes with the respective features is based on at least one of a silhouette score of the feature space and a concordance index.

7. The method of claim 6, wherein the feature subset consists essentially of:
    the measurement of lymphocyte areas of the image,
    the measurement of tumor-infiltrating lymphocyte areas of the image,
    the measurement of tumor-adjacent lymphocyte areas of the image, and
    the measurement of tumor-infiltrating stroma areas of the image.

8. The method of claim 1, wherein the instructions further cause the apparatus to:
    apply a Cox proportional hazards model to clinical features of the tumor to determine a class of the tumor, and
    determine the clinical value for the individual based on prognoses of the individuals with tumors in the class into which the classifier classified the tumor and the class determined by the Cox proportional hazards model.

9. The method of claim 8, wherein the clinical features of the tumor of the Cox proportional hazards model are selected from a clinical feature set including:
    a primary diagnosis of the tumor,
    a location of the tumor,
    a treatment of the tumor,
    a measurement of the tumor,
    a metastatic condition of the tumor,
    a primary diagnosis of the individual,
    a previous cancer medical history of the individual,
    a race of the individual,
    an ethnicity of the individual, a gender of the individual,
a smoking habit frequency of the individual,
a smoking habit duration of the individual, and
an alcohol history of the individual.

10. The method of claim 9, wherein, from the clinical feature set, a clinical feature subset of features is selected for the Cox proportional hazards model based on a correlation of the respective classes with respective clinical features of the clinical feature subset, and the clinical feature subset consists of the measurement of the tumor and the metastatic condition of the tumor.

11. The method of claim 1, wherein:
the at least two classes are a low-risk tumor class and a high-risk tumor class,
determining the lymphocyte distribution further comprises applying a convolutional neural network to the image, the convolutional neural network configured to measure the lymphocyte distribution of lymphocytes for different area types of the image,
the classifier is a two-way Gaussian mixture model configured to determine, for respective classes, a probability distribution of features for tumors in the class within a feature space,
the method further comprises applying a Cox proportional hazards model to clinical features of the tumor to determine a class of the tumor, and
determining the clinical value for the individual is further based on the class determined by the Cox proportional hazards model.

12. The method of claim 1, wherein the instructions further cause the apparatus to display a Kaplan Meier survivability projection of the clinical value for the individual.

13. The method of claim 1, wherein the instructions further cause the apparatus to determine at least one of:
a diagnostic test for the tumor based on the clinical value for the individual;
a treatment of the individual based on the clinical value for the individual; and
a schedule of a therapeutic agent for treating the tumor based on the clinical value for the individual.

14. An apparatus comprising:
a memory storing instructions; and
processing circuitry configured by execution of the instructions stored in the memory to determine a clinical value for an individual based on a tumor in an image by:
determining a lymphocyte distribution of lymphocytes in a tumor based on an image of the tumor,
applying a classifier to the lymphocyte distribution to classify the tumor, the classifier configured to classify tumors into a class selected from at least two classes associated with lymphocyte distributions, and
outputting the clinical value based on prognoses of individuals with tumors in the class into which the classifier classified the tumor, wherein,
the at least two classes are a low-risk tumor class and a high-risk tumor class,
determining the lymphocyte distribution further comprises applying a convolutional neural network to the image, the convolutional neural network configured to measure the lymphocyte distribution of lymphocytes for different area of the image,
the classifier includes a two-way Gaussian mixture model configured to determine, for respective classes, a probability distribution of features for tumors in the class within a feature space, and
the instructions further cause the processing circuitry to,
apply a Cox proportional hazards model to clinical features of the tumor to determine a class of the tumor, and
determine the clinical value for the individual based on the prognoses of the individuals with tumors in the class into which the classifier classified the tumor and the class determined by the Cox proportional hazards model.

15. A non-transitory computer-readable medium storing instructions that, when executed by processing circuitry, cause the processing circuitry to determine a clinical value for an individual based on a tumor in an image by:
determining a lymphocyte distribution of lymphocytes in a tumor based on an image of the tumor,
applying a classifier to the lymphocyte distribution to classify the tumor, the classifier configured to classify tumors into a class selected from at least two classes associated with lymphocyte distributions, and
outputting the clinical value for the individual based on prognoses of individuals with tumors in the class into which the classifier classified the tumor, wherein
the at least two classes are a low-risk tumor class and a high-tumor class,
determining the lymphocyte distribution further comprises applying a convolutional neural network to the image, the convolutional neural network configured to measure the lymphocyte distribution of lymphocytes for different types of the image,
the classifier includes a two-way Gaussian mixture model configured to determine, for respective classes, a probability distribution of features for tumors in the class within a feature space, and
the instructions further cause the processing circuitry to,
apply a Cox proportional hazards model to clinical features of the tumor to determine a class of the tumor, and
determine the clinical value for the individual based on the prognoses of the individuals with tumors in the class into which the classifier classified the tumor and the class determined by the Cox proportional hazards model.

16. A method of operating an apparatus including processing circuitry and a convolutional neural network that is trained to determine a lymphocyte distribution of lymphocytes in an area of an image, the method comprising:
executing, by the processing circuitry, instructions that cause the apparatus to:
receive an image depicting at least part of a tumor,
invoke the convolutional neural network to determine a lymphocyte distribution of lymphocytes in respective areas of the tumor based on the image,
apply a classifier to the lymphocyte distribution to classify the tumor, the classifier trained to classify tumors into a class selected from at least two classes associated with lymphocyte distributions, and
determine a clinical value for an individual based on a set of prognosis data corresponding to individuals with tumors in the class into which the classifier classified the tumor,
wherein the convolutional neural network is further trained to classify an area of the image as one or more area types selected from an area type set including a tumor area, a lymphocyte area, and a stroma area, wherein determining the lymphocyte distribution of lymphocytes in the tumor includes, for respective stroma areas of the image,
- determining a distance of the stroma area to a tumor area, and
- based on the distance, characterizing the stroma area as one of a tumor-infiltrating stroma area, and a tumor-adjacent stroma area, and wherein the classifier is configured to further classify the tumor based on the characterizing of the stroma area.

* * * * *